US006592526B1

(12) United States Patent
Lenker

(10) Patent No.: US 6,592,526 B1
(45) Date of Patent: *Jul. 15, 2003

(54) RESOLUTION ULTRASOUND DEVICES FOR IMAGING AND TREATMENT OF BODY LUMENS

(76) Inventor: Jay Alan Lenker, 408 Panorama Dr., Laguna Beach, CA (US) 92651

( * ) Notice: Subject to any disclaimer, the term of this patent is extended or adjusted under 35 U.S.C. 154(b) by 286 days.

This patent is subject to a terminal disclaimer.

(21) Appl. No.: 09/690,795

(22) Filed: Oct. 17, 2000

Related U.S. Application Data

(63) Continuation-in-part of application No. 09/632,317, filed on Aug. 4, 2000, now abandoned, which is a continuation-in-part of application No. 09/236,936, filed on Jan. 25, 1999, now Pat. No. 6,110,121.

(51) Int. Cl.$^7$ ................................................ A61B 8/12
(52) U.S. Cl. ........................................ 600/463; 600/466
(58) Field of Search .............................. 600/463, 437, 600/443, 454, 462, 466–467, 471; 128/916

(56) References Cited

U.S. PATENT DOCUMENTS

| 4,587,972 | A | 5/1986 | Morantte, Jr. |
| 4,776,337 | A | 10/1988 | Palmaz |
| 4,917,085 | A | 4/1990 | Smith |
| 4,917,097 | A | 4/1990 | Proudian et al. |
| 5,000,185 | A | 3/1991 | Yock |
| 5,030,201 | A | 7/1991 | Palestrant |
| 5,109,859 | A | 5/1992 | Jenkins |
| 5,125,410 | A | 6/1992 | Misono et al. |
| 5,135,531 | A | 8/1992 | Shiber |
| 5,243,988 | A | 9/1993 | Sieben et al. |
| 5,313,949 | A | 5/1994 | Yock |
| 5,377,685 | A | 1/1995 | Kazi et al. |
| 5,379,772 | A | 1/1995 | Imran |
| 5,405,337 | A | 4/1995 | Maynard |
| 5,421,338 | A | 6/1995 | Crowley et al. |
| 5,485,845 | A | 1/1996 | Verdonk et al. |
| 5,498,227 | A | 3/1996 | Mawad |

(List continued on next page.)

OTHER PUBLICATIONS

Krulevitch, et al., Thin Film Shape Memory Alloy Microactuators, Journal of Microelectromechanical Systems, Dec. 1996, p. 270–282 vol. 5 No. 4.

Van Urk et al., Endovascular Ultrasound, p. 29–35, Vascular and Endovasular Surgical Techniques, 3rd ed., RNGreenhalgh, Editor, WB Saunders, London, England, 1994.

EndoSonics, Solid–State Intracoronary Ultrasource A Technolog Whose Time Has Come, p. 1–4, http://www.endosonics.com/reference/solid.htm.

Primary Examiner—Francis J. Jaworski

(57) ABSTRACT

A rotationally vibrating imaging catheter and method of utilization has an array of ultrasound transducers and an actuator along with signal processing, display, and power subsystems. The actuator of the preferred embodiment is a solid-state nitinol actuator. The actuator causes the array to oscillate such that the tip of the catheter may be rotated through an angle equal to or less than 360 degrees. The tip is then capable of rotating back the same amount. This action is repeated until the desired imaging information is acquired. The rotationally vibrating catheter produces more imaging points than a non-rotating imaging catheter and eliminates areas of missing information in the reconstructed image.

Rotationally vibrating catheters offer higher image resolution than stationary array catheters and greater flexibility and lower costs than mechanically rotating imaging catheters.

The rotationally vibrating array carried on a catheter may also be vibrated or rocked forward and backward to allow for acquisition of three-dimensional information within a region around the transducer array.

The addition of adjunctive therapies to the imaging catheter enhances the utility of the instrument. Examples of such therapies include atherectomy, stent placement, thrombectomy and irradiation.

21 Claims, 16 Drawing Sheets

U.S. PATENT DOCUMENTS

| | | |
|---|---|---|
| 5,505,088 A | 4/1996 | Chandraratna et al. |
| 5,546,948 A | 8/1996 | Hamm et al. |
| 5,575,772 A | 11/1996 | Lennox |
| 5,588,432 A * | 12/1996 | Crowley .................... 600/439 |
| 5,606,975 A | 3/1997 | Liang et al. |
| 5,651,366 A | 7/1997 | Liang et al. |
| 5,657,760 A | 8/1997 | Ying et al. |
| 5,699,805 A | 12/1997 | Seward et al. |
| 5,720,285 A | 2/1998 | Petersen |
| 5,735,282 A | 4/1998 | Hossack |
| 5,766,192 A | 6/1998 | Zacca |
| 5,771,896 A | 6/1998 | Sliwa, Jr. et al. |
| 5,779,643 A | 7/1998 | Lum et al. |
| 5,899,882 A | 5/1999 | Waksman et al. |
| 5,924,973 A | 7/1999 | Weinberger |
| 5,980,554 A | 11/1999 | Lenker et al. |
| 5,989,243 A | 11/1999 | Goldenberg |
| 6,007,573 A | 12/1999 | Wallace et al. |
| 6,013,033 A | 1/2000 | Berger et al. |
| 6,077,213 A | 6/2000 | Ciezki et al. |
| 6,110,121 A | 8/2000 | Lenker |
| 6,119,031 A * | 9/2000 | Crowley .................... 600/407 |

* cited by examiner

RESOLUTION ULTRASOUND DEVICES FOR IMAGING AND TREATMENT OF BODY LUMENS

This application is a continuation-in-part of U.S. application Ser. No. 09/632,317, filed on Aug. 4, 2000, now abandoned, which is a continuation-in-part of U.S. application Ser. No. 09/236,936, filed on Jan. 25, 1999, now U.S. Pat. No. 6,110,121.

FIELD OF INVENTION

This invention relates to improvements in devices for intravascular ultrasound (IVUS) guided catheter systems.

BACKGROUND OF INVENTION

Intravascular ultrasound is a rapidly evolving imaging technique most commonly employed in coronary and iliofemoral arteries. The technique has the potential to facilitate the study of aneurysm progression, atherosclerosis or dissection and to outline the effect of endovascular intervention in more detail than angiography.

The presently used intravascular ultrasound systems fall into two categories: stationary electronic systems and mechanically driven rotating transducer systems. In both systems, an acoustic element or transducer is used to transmit a signal, which impinges upon, and reflects from, surfaces of different acoustic densities, which the signal encounters. An acoustic transducer receives the reflected wave. These data are sent to a processing system via an electrical cable where they are manipulated and displayed as an image. The systems are mounted to catheters, or axially elongate structures, which are routed through body lumens such as arteries to reach the site of imaging.

The non-rotating or stationary catheter of the stationary electronic system houses an array of small acoustic elements, which are positioned cylindrically at the catheter tip. After positioning the catheter in a vessel, body lumen or cavity, subgroups of acoustic elements may together generate an echo image. The spacing between the acoustic elements in the transducer array creates areas where the acoustic signal is neither transmitted nor received. When the data is processed, gaps of missing information occur, resulting in a poor quality image. The advantage of the stationary electronic system is that the catheter is very flexible and a central lumen is available for guidewire insertion. No distortion of the image, due to inhomogeneous mechanical rotation, is present. The stationary catheters are reliable and inexpensive but produce a poor quality image.

The mechanical intravascular ultrasound-imaging catheter comprises a mechanically rotating catheter shaft with a single ultrasound transducer. Either the acoustic element rotates or the acoustic element is stationary and a mirror rotates. In this manner, the acoustic signal is transmitted and received in a continuous 360-degree sweep. There are no gaps in the data and a higher quality image results. Realizing a driving mechanism while keeping the catheter fully flexible and steerable as well as miniature are challenging problems. Distortion of the image due to an unequal rotation of the element or mirror at the catheter tip is a limitation of these systems. Advantages of the mechanical probes include high-resolution imaging and absence of near field artifact. The mechanically rotating devices produce an acceptable image but are unreliable and expensive.

Both stationary electronic systems and mechanical systems typically operate with acoustic frequencies from 10 to 30 MHz.

Medical interventions are often performed using endovascular techniques. These interventions include balloon dilatation, atherectomy, stent or device placement and removal, drug delivery, thrombolytic therapy, thrombectomy, vessel irradiation, embolic device delivery and thermal therapy by radio waves or microwaves. Guidance of these endovascular interventions is preferably accomplished using intravascular ultrasound imaging.

The present invention, using a solid-state actuator, is more reliable and less expensive than the rotating catheters with a single acoustic transducer. It can also easily have a central lumen for instrumentation or for a guidewire. In addition, the present invention produces a higher resolution image with fewer gaps in the information than the stationary imaging catheters. This invention creates a high-resolution ultrasound image with higher reliability and less expense than is currently available. This invention has the ability to generate real-time three-dimensional ultrasound images of the region surrounding the acoustic transducers.

Another significant advantage of the present invention is its ability to navigate tortuous vasculature in order to reach the site of the lesion in the body vessel or lumen. It is, because of its greater flexibility, useful in catheters used to treat lesions of the cerebrovasculature or distal coronary circulation. Interventional devices, delivering therapies such as atherectomy, thrombectomy and irradiation, stent placement or removal, thrombogenic therapy and thrombolytic therapy, guided by this high-resolution ultrasound system, offer improved guidance and precision of placement as well as flexibility at potentially reduced cost and higher reliability than that obtainable from rotating shaft devices. Thus, this invention fills a market demand for a high resolution, reliable and inexpensive imaging and therapeutic catheter.

SUMMARY OF INVENTION

The present invention is a catheter comprising an array of ultrasound transducers and actuators along with signal processing, display, and power subsystems. The actuators on the catheter cause the array to oscillate. This allows the array to produce more imaging points of the object to be viewed than a non-rotating or a stationary array. Additional computer processing of the ultrasound data produces an image with a higher resolution than images produced from data from a non-oscillating transducer array.

The present invention comprises a catheter, or axially elongate structure, which has a distal tip and a proximal end. The catheter optionally comprises a central lumen or a guidewire tip. The central lumen is often used for guidewire passage. It may also comprise additional lumens for purposes such as balloon inflation and deflation, stent deployment, device retrieval, contrast media or material injection, electromagnetic emissions and drug injection or removal. The distal tip comprises an array of at least one transducer for transmitting ultrasound energy radially outward, an array of at least one transducer for receiving ultrasound signals, and one or more actuators. The transmitting and receiving transducers may optionally be the same physical entity. The transmitting and receiving transducers are electrically connected to the proximal end of the catheter by a transmission line, cable or wire bundle, which is electrically connected to a decoder, a power generator, and a display instrument. The actuators are also electrically connected to the proximal end of the catheter with a transmission line, cable or wire bundle, which is electrically connected to a power supply. The ultrasound transducer array on the distal tip of the catheter transmits and receives ultrasound signals, which are processed by a computer to create an image of the object subjected to the ultrasound signals.

The transducer array, located near the distal tip of the catheter, rotates clockwise and then counterclockwise either with the rest of the catheter or, preferably independent of the catheter. The array may be rotated through an angle equal to or less than 360 degrees. Most advantageously, the array is rotated sufficiently to fill in the information gaps but not more than required to minimize the requirements of the actuator and linkages. The array is then capable of rotating backwards the same amount. The net motion is a rotating oscillation or a vibration. The oscillating array may be optionally covered with a non-oscillating shield. Preferentially, the array will be rotated much less than 360 degrees so multiple transducers are required in the array to maintain a full field of view.

In one embodiment, the distal tip of the catheter comprises an imaging array that is directed forward as well as the imaging array that is directed radially outward. The forward directed array allows for acquisition of additional information on the vessel distal to the catheter.

The present invention does not continually rotate. It vibrates rotationally in the same manner as an agitator to gather data to fill in the missing information between array elements. The rotating array allows for imaging of a two-dimensional "slice of pie"- or wedge-shaped segment of the lumen and surrounding tissue. This two-dimensional imaging region is orthogonal to the axis of the array and generally orthogonal to the axis of the catheter. By circumferentially vibrating, the array is caused to move to fill in any gaps in information that exist between adjacent array elements. Lost information between array elements is the reason stationary array systems offer less resolution than rotating transducer systems.

Since the movement of the array occurs only near the tip of the catheter, the catheter can be made very flexible up to the point of the array and, thus, able to negotiate tortuous vasculature. Stiff drive cables used for rotational systems would not pass through tight curves and could not function distal to serpentine or highly tortuous vascular pathways. The actuators and array of the present invention can be made very small to accommodate high flexibility requirements of catheters needed to navigate tortuous vasculature and still function.

In one embodiment of the present invention, the transducer array is oscillated circumferentially, and in addition, rocked back and forth along the axis of the catheter to provide imaging information in three-dimensional space around at least a portion the tip. Actuators rotate the array circumferentially as well as axially, with respect to the axis of the catheter, to create a pyramidal-shaped imaging volume with a spherical exterior around each transducer of the array. The three-dimensional information is also obtainable in a spherical volume around the transducer array when it is designed with overlapping fields of view.

The preferred embodiment for vibrating or agitating the distal tip of the catheter is a nitinol actuator or sets of nitinol actuators mounted to cause movement of the transducer array. When the nitinol is exposed to electrical current, it changes dimensions due to resistive heating. When the electric current is removed, the nitinol returns to its original dimensions. Allowance for hysteresis must be made. By counter-attaching the actuators, they can be alternately activated and deactivated causing the transducer array to alternately vibrate clockwise and then counterclockwise or to pivot forward and backward axially. This type of actuator may be used for back and forth motion of the array along the axis of the catheter as well as circumferential motion. The actuator set may be built with separate actuators or as a single system capable of moving the array through two-dimensions to create the three-dimensional image. Counter-attached actuators could also be replaced with a single actuator using a spring return or other mechanism to ensure correct reverse motion when the power is turned off to the single actuator.

In another embodiment, the invention includes apparatus for cutting or excising atheroma, thrombus or other tissue from the interior of the body vessel or lumen. This apparatus comprises an actuator, which may or may not be the same as that which drives the imaging array, and cutting elements that act to cut tissue. The cutting elements may be disposed within a window on the side of the catheter to perform directional atherectomy or thrombectomy. The cutting elements may also be disposed in the forward direction to allow for channeling when the catheter is advanced. The invention also comprises catheter lumen structures and systems to provide suction to assist in the removal of the excised material.

In yet another embodiment, the invention comprises apparatus for illuminating the body vessel or lumen with electromagnetic radiation at wavelengths from gamma rays to radio waves. Visible light delivery may be accomplished using fiber-optic channels to transmit light in the visible, infrared or ultraviolet range. Ionizing radiation may be generated from a radioactive source, such as Iridium 192, Iodine 131, Iodine 125, Palladium 109, Strontium 90, Cobalt 57 and Cobalt 60, mounted to the tip of the catheter. Examples of ionizing radiation are electrons, positrons, beta particles, gamma rays and X-rays. A removable shield may be provided to allow irradiation only at the desired site. A microwave, X-ray or radio frequency (RF) wave source may also be mounted to the tip of the catheter. Power for the X-ray source, microwave or RF transducer is carried through the catheter by an electrical cable, wires or group of wires.

In another embodiment, the invention comprises a catheter capable of deploying or retrieving a device such as a stent, balloon dilator or vaso-occlusive material while monitoring the deployment or its result with the imaging array. In this embodiment, the array might be internal to the catheter or external to the catheter. The catheter may be placed through the lumen of one or more guiding catheters to facilitate maneuvering of the catheter tip through the vasculature or other body lumen.

The two-dimensional image is processed and displayed, preferentially in real time, on a two-dimensional monitor. The three-dimensional image is processed using standard techniques and displayed, preferentially in real time, by mapping the image to a two-dimensional monitor. Three-dimensional systems such as holographic projectors may allow for full three-dimensional modeling. The key to processing of the image is coordination of instant array element position with its one-dimensional ultrasound mapping information. Moving the transducer in one dimension makes a two-dimensional image and moving the transducer in two dimensions results in three-dimensional information.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

DETAILED DESCRIPTION OF THE INVENTION

The invention herein described is an ultrasound imaging and treatment catheter comprising a rotationally vibrating array of ultrasound transducers. The catheter of the present invention allows the flexibility and cost effectiveness of a conventional stationary ultrasound-imaging catheter but has superior image data gathering capabilities as is illustrated in FIGS. 1, 2A, and 2B.

Figure 1:
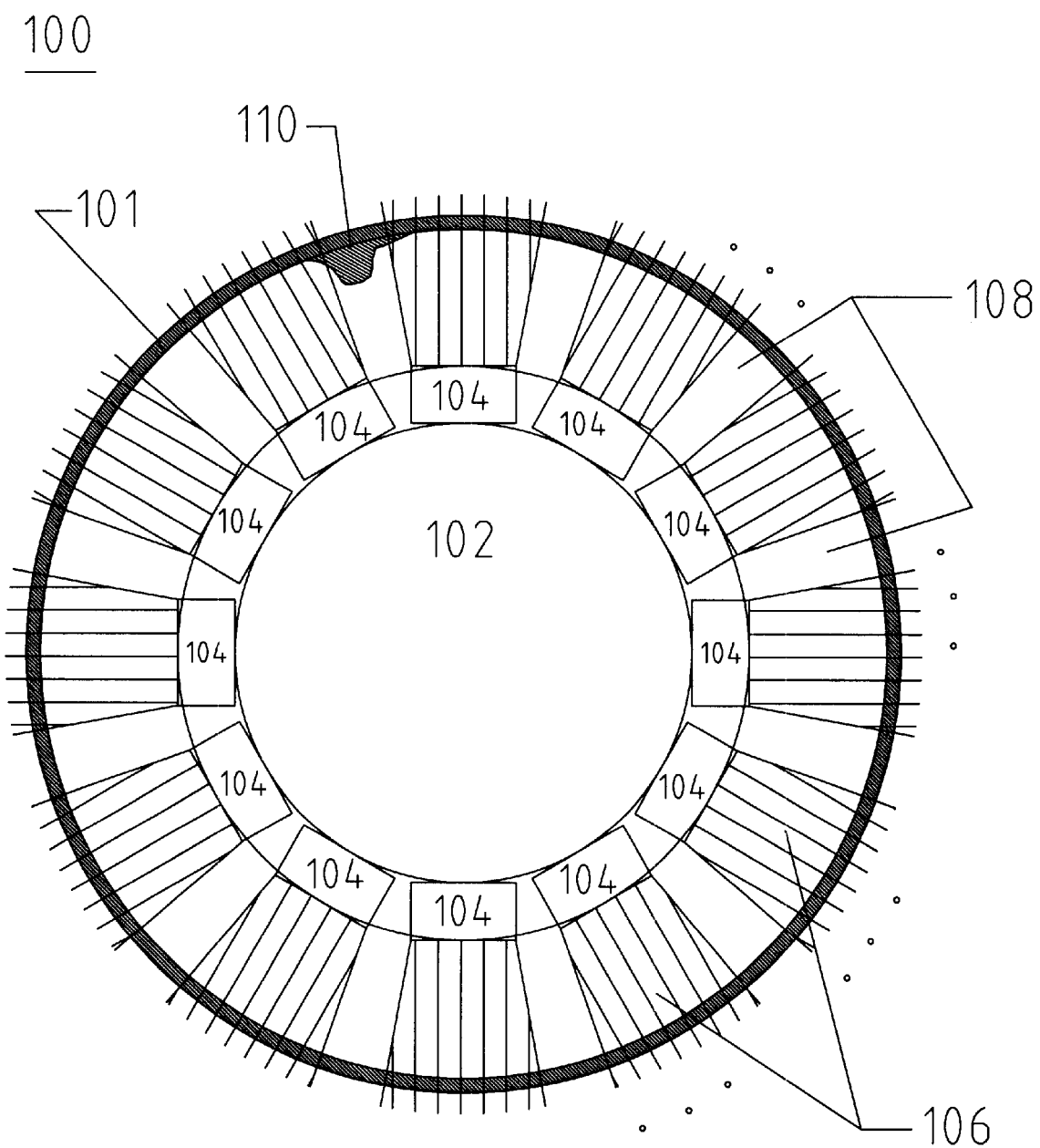
FIG. 1 shows the imaging area for a stationary imaging catheter positioned in a body lumen, according to aspects of an embodiment of the invention.

FIG. 1 illustrates, in cross section, a distal tip of a stationary imaging catheter 102 imaging a body lumen 100. The body lumen 100 has an inside surface irregularity 110 on a body lumen wall 101. The imaging catheter 102 comprises a plurality or array of ultrasound transducers 104, a plurality of fields of view or imaging areas 106 and a plurality of blind spots or blind areas 108. Examples of body lumens include arteries, veins, ureters, the bladder, the urethra and biliary ducts. The transducers 104 are placed circumferentially around the tip 102. Each transducer 104 transmits ultrasound energy and receives reflected ultrasound energy within its field of view 106. The blind spots 108 are areas where no ultrasound energy is transmitted nor is any reflected ultrasound energy received. Most of the illustrated lumen irregularity 110 is in one of the blind spots 108. After data from the transducers 104 is processed to create a visual image, the blind spots 108 correspond to areas of no or missing information, resulting in a poor image.

Figure 2A:
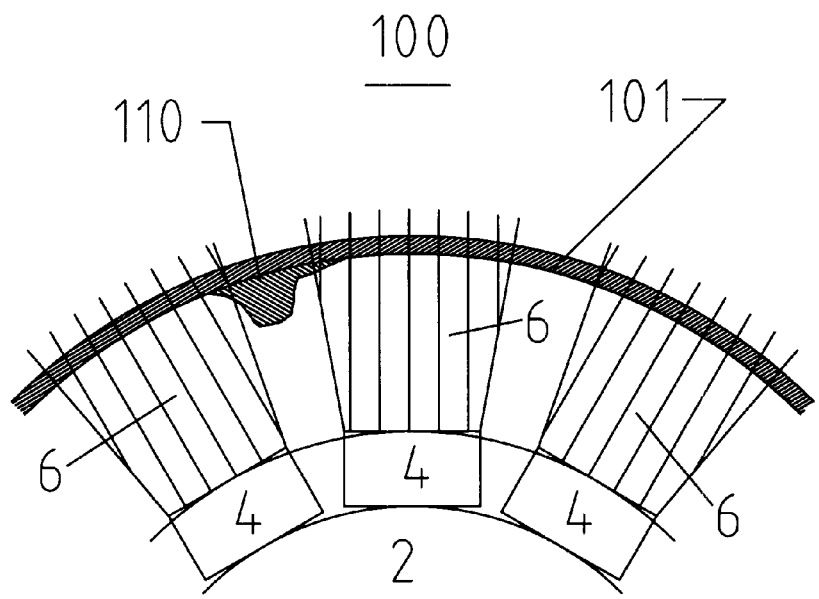
FIGS. 2A and 2B show the imaging area for a vibrating imaging catheter of the present invention, positioned in a body lumen, according to aspects of an embodiment of the invention.

Referring to FIG. 2A, a circumferentially vibrating portion of a distal tip or end 2 of an imaging catheter images a portion of the body lumen 100. The vibrating part of the imaging catheter comprises a plurality or array of ultrasound transducers 4, and a plurality of fields of view or imaging areas 6. The transducers 4 are placed circumferentially around the tip 2. Each transducer 4 transmits output ultrasound acoustic waves or energy in response to output or transmission electrical signals and receives reflected ultrasound energy within its imaging area 6. The surface irregularity 110 of the body lumen 100 is not yet in the imaging area 6 of the transducers 4.

Figure 2B:
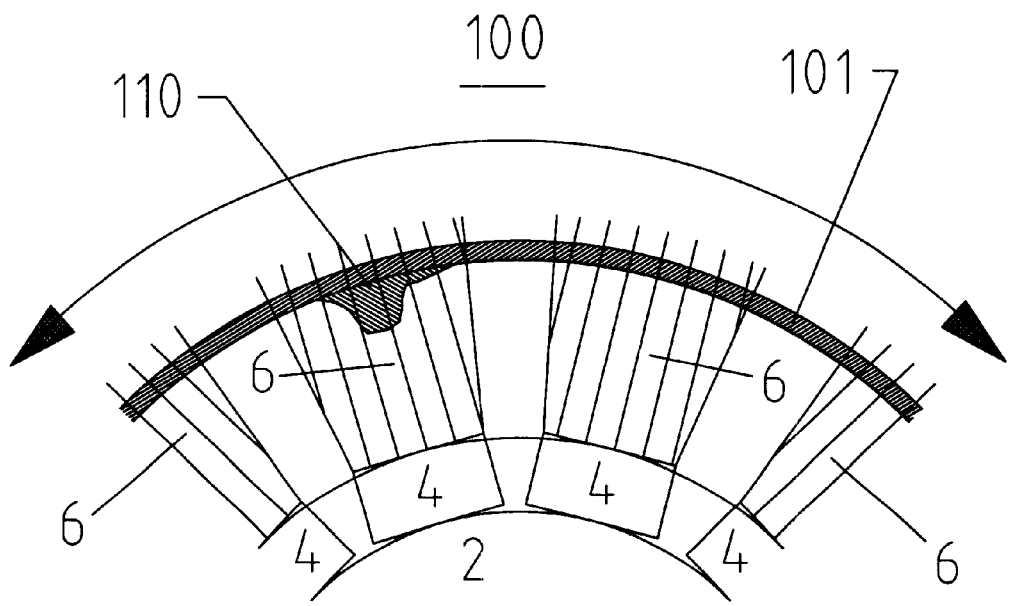

As the array of transducers 4, located within or on the catheter tip 2 is circumferentially vibrated, as illustrated in FIG. 2B, the transducers 4 continue to transmit output ultrasound acoustic waves to and receive reflected ultrasound energy from the body lumen 100. However, each transducer 4 is circumferentially vibrating and shifted from its previous position. The imaging areas 6 overlap, as shown by comparing FIGS. 2A and 2B. The surface irregularity 110 of the body lumen 100 is in the field of view or imaging area 6 of the transducers 4 after the transducers 4 are circumferentially, or rotationally, vibrated. When the reflection data from the transducers 4 is processed, the resulting visual image has no areas of missing information; thus resulting in a complete image, which is superior to the image produced by a stationary ultrasound catheter.

Figure 3:
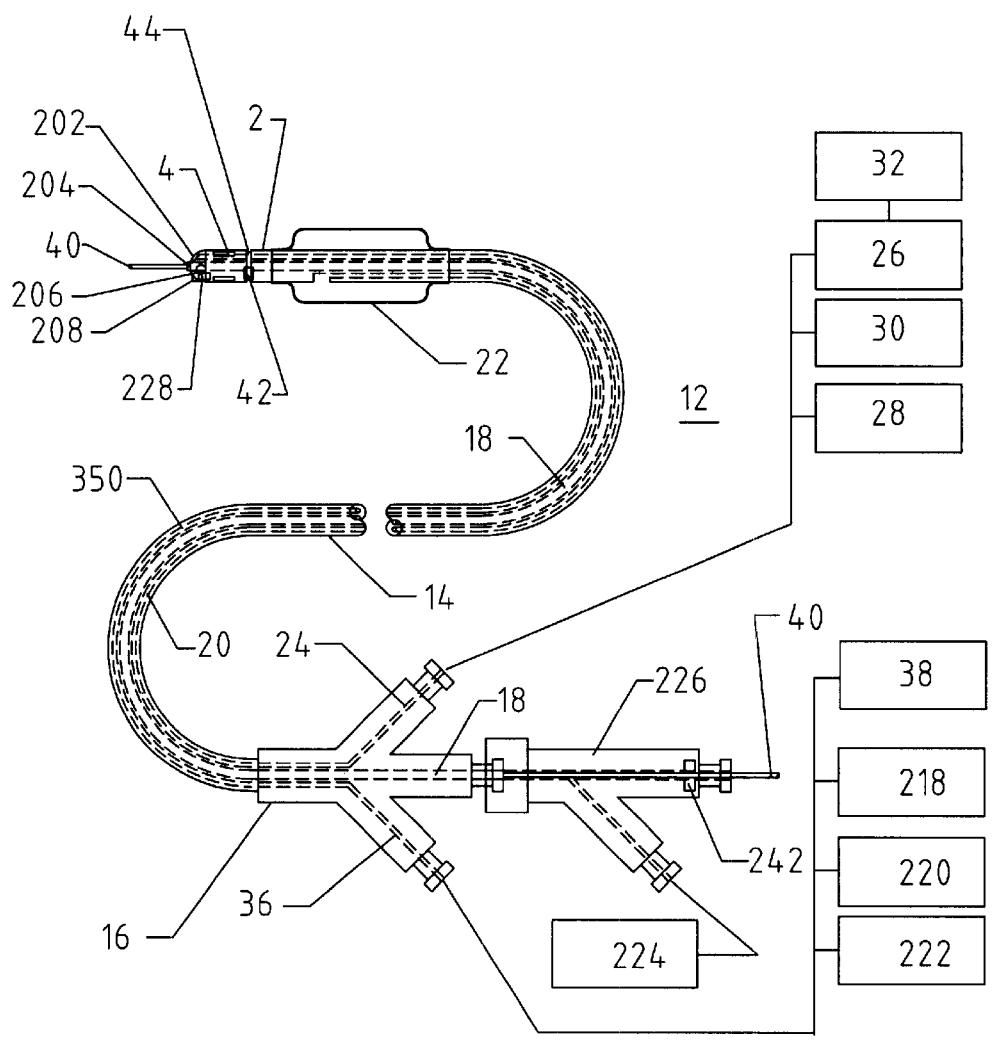
FIG. 3 is a schematic view of an intravascular ultrasound catheter with optional therapeutic apparatus mounted thereto, according to aspects of an embodiment of the invention.

The device of the present invention, as shown in FIG. 3, is a catheter 12 comprising a catheter shaft 14, a proximal end 16, the distal end or tip 2, a central lumen 18 and a wire bundle or transmission line 20. Additional lumens may optionally be added for functions such as dye or fluid injection, fluid removal, electrical or electromagnetic energy delivery, atherectomy control, stent or material deployment or retrieval, balloon inflation and/or deflation. The proximal end 16 comprises a power/data port 24, a decoder/processor system 26, an ultrasound-input signal and power supply/controller 28, an actuator power supply/controller 30, and a display device or display monitor 32. The proximal end 16 optionally comprises an inflation port 36, an inflation lumen 350, an inflation system 38 and a guidewire 40. The inflation system 38 may, for example, be a syringe with or without mechanical advantage such as levers or jackscrews. The proximal end 16 further optionally comprises an illumination source 218, a power source 220 for X-ray, radio frequency or microwave energy and/or a shutter controller 222 for an ionizing radiation source. A connector 226 is optionally provided at the proximal end of the catheter 12 to seal the guidewire 40 entrance against fluid leakage, using a proximal fluid-tight seal 242, and to allow for attachment of a suction device or vacuum source 224 to remove fluid and excised debris from the body vessel or lumen. Fluid injection to the body lumen may be for purposes such as occlusion, chelation, drug delivery or lysis.

Additionally, the distal tip 2 comprises the plurality or array of radially, outwardly directed ultrasound transducers 4, a circumferential actuator 42 or, in the preferred embodiment, a nitinol circumferential actuator 42, and a swivel joint or circumferential rotational bearing 44. The distal tip further optionally comprises the other end of the central lumen 18, the other end of the guidewire 40, or a balloon 22. The balloon 22 may be an angioplasty-type balloon suitable for vessel dilation or stent expansion. Such balloons are made from materials such as polyethylene terephthalate (PET), polyimide or other high-strength polymers. The balloon 22 could also be made from elastomeric materials like polyurethane or latex. Such materials may be suited for centering the catheter tip in the body lumen or vessel.

The distal tip 2 of catheter 12 optionally comprises an array of forwardly directed ultrasound transducers 202. It also optionally comprises a distal fluid-tight seal 204, which prevents fluid from passing into the central lumen 18 from the guidewire 40 exit. A cutting apparatus 208 and a fluid suction or vacuum port 206 are also included on the oscillating distal tip 2 of the catheter. The distal tip 2 of catheter 12 further optionally comprises a wave source 228. Possible wave sources are X-ray emitters, microwave and radio frequency antennas and ionizing radiation sources.

Figure 4:
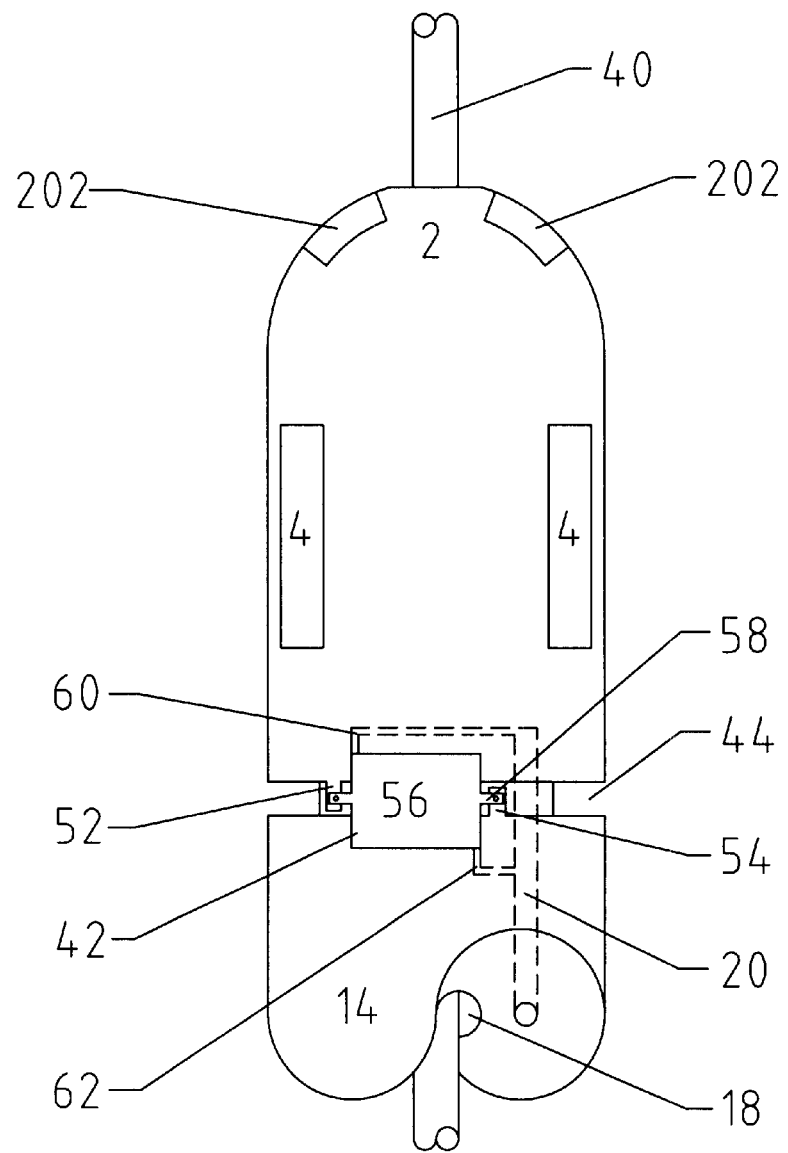
FIG. 4 is an enlarged detail of the distal tip of the imaging catheter of FIG. 3 illustrating the actuator of the preferred embodiment with a radially directed ultrasound array and an optional forwardly directed ultrasound array, according to aspects of an embodiment of the invention.
Figure 5:
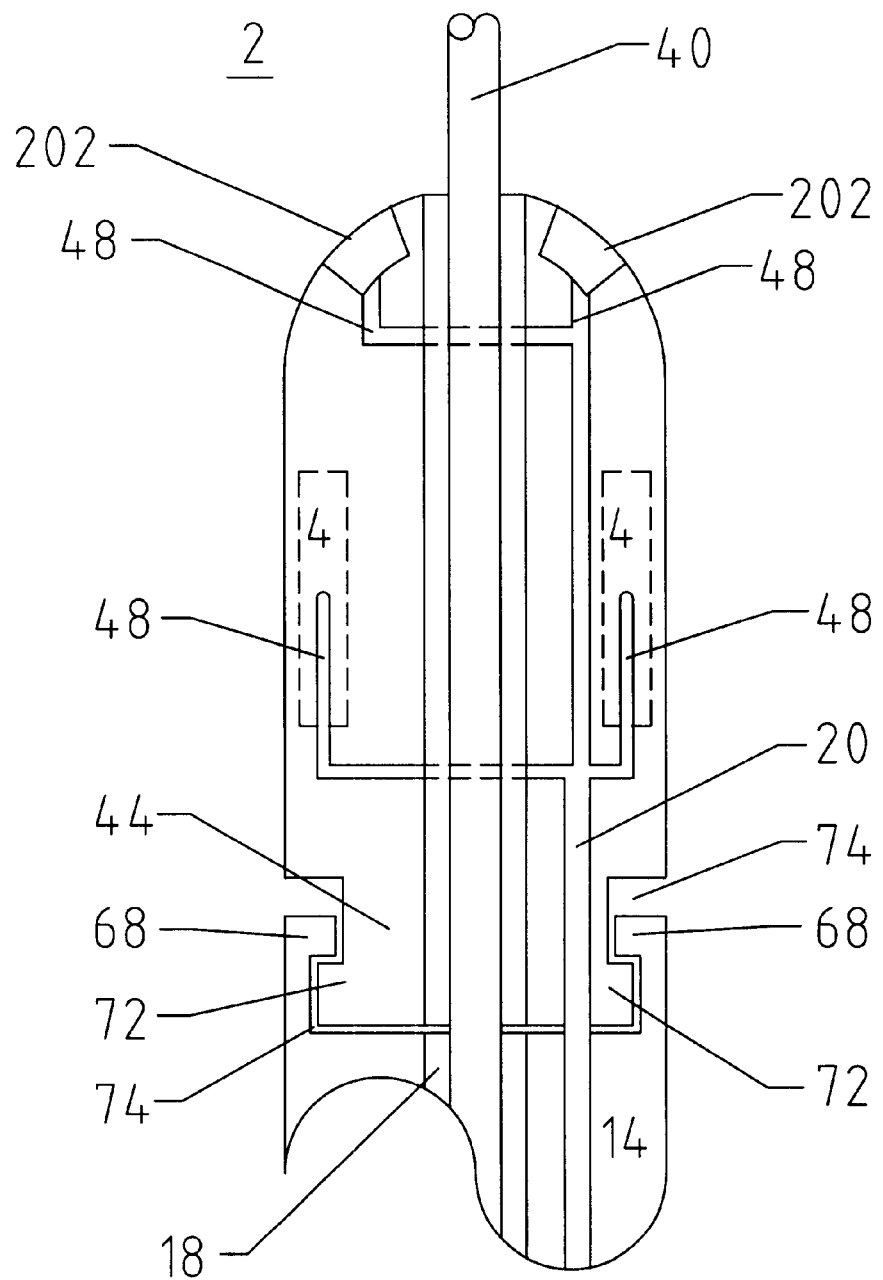
FIG. 5 is an enlarged sectional view of the distal tip of the catheter of FIG. 3 illustrating the forward directed and radially outwardly directed ultrasound transducer arrays, electrical connections and the swivel connection, according to aspects of an embodiment of the invention.

As shown in FIG. 5, each transducer in the transducer arrays 4 and 202 comprises a plurality of transducer leads 48. As shown in FIG. 4, the circumferential actuator 42 comprises a positive signal/power lead 60 and a negative signal/power lead 62. The leads 48, 60, 62 are bundled together in the wire bundle or transmission line 20 which travels the length of the catheter shaft 14 and carries power to the actuator 42 as well as output and reflection electrical signals to and from, respectively, the acoustic arrays 4 and 202. The central lumen 18 is also shown.

Referring to FIG. 3, the catheter 12 is positioned in a body lumen or cavity to collect data for an ultrasound image. The lumen wall ideally fits against the outside of the catheter or is liquid-filled in order to efficiently transmit the acoustic waves. In lumens that are not liquid filled, the balloon 22 may be disposed to surround transducers 4 and inflated with liquid to fill the space between the catheter tip 2 and wall of the body lumen. The ultrasound array signal and power supply/controller 28 sends output signals to and receives reflection signals from the transducer arrays 4 and 202 over the cable or wire bundle 20. The information from the ultrasound arrays 4 and 202, in the form of reflection electrical signals, is sent to the decoder/processor system 26 where the electronic data is processed to compensate for jitter, hysteresis, and uneven rotation. The processed data is sent to the display monitor 32 where the ultrasound image of the body lumen or cavity is displayed.

While the ultrasound arrays 4 and 202 are receiving and transmitting information, the circumferential actuator 42 is receiving control signals from the actuator power supply 30. The actuator control signals are such so as to cause the circumferential actuator 42 to rotate the distal tip 2 of the catheter 12 through an angle of 360 degrees or less and then reverse the rotation through an angle of 360 degrees or less. Once the clockwise and counterclockwise rotation cycle is complete, the cycle repeats until the desired data is collected.

In a preferred embodiment, the circumferential actuator 42 utilized to rotationally vibrate the distal tip 2 of the ultrasound-imaging catheter 12 is a nitinol actuator. Nitinol is a nickel-titanium alloy, which may exhibit a shape memory effect. Shape memory alloys (SMA) are easily deformed and, when heated, they return to their original shape. Shape memory actuators fabricated from thin film or wire can be heated resistively. The small thermal mass and large surface to volume ratios associated with thin films allow for rapid heat transfer. Switching rates can be in the range of up to about 100 Hz or faster. Motion rates for transducers 4 ideally will be between 1 Hz and 300 Hz and more preferentially between 30 Hz and 200 Hz in order to provide an image with a minimum of flicker.

FIG. 4 shows the distal tip 2 of the catheter 12 of FIG. 3 with the circumferential actuator 42 of the preferred embodiment. The distal tip 2 of the catheter comprises the central lumen 18 with the guidewire 40, the ultrasound transducer array 4, the swivel joint 44, the wire bundle 20 and the nitinol actuator 42. Optionally, the distal tip 2 also contains the forwardly directed ultrasound transducer array 202. The nitinol actuator 42 comprises a mount top 52 and a mount bottom 54, a nitinol ligament/element 56, a connection or attachment 58, the positive signal/power lead 60 and the negative signal/power lead 62. The mount bottom 54 is attached to the catheter shaft 14 while the mount top 52 is attached to the catheter tip 2. The positive lead 60 and the negative lead 62 are attached to opposite edges of the nitinol ligament/element 56, respectively.

Referring to FIG. 3 and FIG. 4, the positive lead 60 and the negative lead 62 are routed into the wire bundle or transmission line 20. The positive 60 and negative leads 62 exit the wire bundle 20 at the power/data port 24 where they are connected to the actuator power supply/controller 30. The actuator power supply/controller 30 transmits over the transmission line 20 an electrical signal through the leads 60, 62 to the nitinol ligament/element 56. This creates either resistive heating when powered or cooling when power is removed through the nitinol ligament/element 56 which causes the nitinol ligament/element 56 to expand or contract its length along the circumference of the distal tip 2.

The nitinol ligament 56 comprises a nitinol film attached to a flexible substrate as described by R. S. Maynard in U.S. Pat. No. 5,405,337. The nitinol film is deposited onto a corrugated silicon surface coated with a thin layer of silicon nitride giving the nitinol ligaments 56 a sinusoidal shape. Polyimide is then spun on and windows are opened to expose the nitinol element. After dissolving the silicon wafer, the flexible polyimide acts as a support structure for the nitinol ligaments 56. While a shape memory alloy actuator is the preferred embodiment, other actuators 42, such as those manufactured with electromagnetic or mechanically driven systems, could also be used. The published literature includes other SMA actuators that are also useable with this invention.

Referring to FIG. 3 and FIG. 4, the actuator power controller 30 sends a signal through the positive 60 and negative leads 62 to the SMA ligament/element 56 such that the ligament/element 56 becomes heated and contracts which pulls or rotates the distal tip 2 through an angle of 360 degrees or less at the swivel joint 44. Next, the power supply/controller 30 sends a signal causing the SMA ligament/element 56 to cool and stretch, which pulls back or reverses the rotation of the distal tip 2 through the swivel joint 44. Typically heating is caused by applying power to the resistive load of the SMA element/ligament and cooling is caused by removing said power. The duty cycle of the signal is set to cause the SMA ligament/element 56 to continuously pull and push the distal tip 2. The resulting motion is a rotational vibration of the catheter tip 2.

In a more preferred embodiment, a plurality of nitinol actuators 42 are disposed circumferentially around the catheter tip 2. The phases of the controlling signals are adjusted such that when one nitinol actuator 42 is pulling, the opposing SMA actuator 42 is pushing. That is, when power is applied across the leads 60 and 62 of the first actuator 42, the electrical power across the electrical leads 60 and 62 of the second SMA actuator 42 is turned off. In this manner, the rotational vibration of the catheter tip 2 can be made steadier and more reliable.

In another embodiment, the actuator 42 is electromagnetic, using permanent magnets and electromagnets to oscillate the catheter tip 2. This system is similar to an electric motor in that the polarities are switched on the electromagnet but continuous rotation is prevented. The electromagnetic system can be installed in the catheter tip 2 or it can transmit the energy through a torque shaft and thus be outside the body.

In yet another embodiment, a mechanical rocker linkage can be used to cause the rotational oscillations.

In another preferred embodiment the tip 2 rotates independently of the catheter shaft 14. A longitudinal section of the distal tip 2 is shown in FIG. 5. The distal tip 2 comprises the plurality or array of radially directed ultrasound transducers 4 and, optionally forwardly directed ultrasound transducers 202, the wire bundle 20, the guidewire 40, and the swivel connection 44. Each transducer 4 and 202 comprises leads 48 which are constrained together in the wire bundle 20. The swivel connection 44 of this embodiment comprises a shaft lip 68, a tip lip 72, and a corresponding void 74. The shaft lip 68, the tip lip 72, and the void 74 are all annular. The shaft lip 68 and tip lip 72 mate in a non-binding manner with the void 74 between the shaft lip 68 and tip lip 72. The shaft lip 68 and tip lip 72 are constructed to retain the distal tip 2 onto the catheter shaft 14. This results in the catheter shaft 14 retaining the catheter tip 2 but allowing the tip 2 to rotate freely on the shaft 14. The wire bundle 20 comprising the leads 48, 60, 62 passes through the above described annular swivel joint 44.

In another embodiment, the leads are connected to a swivel joint electrical rotational connector 44 to allow for the passage of electrical signals and power through the swivel joint.

Yet another embodiment of the swivel joint 44 is an elastic segment joining the catheter shaft 14 and the catheter tip 2. This segment absorbs torque of the oscillating tip 2 and does not transmit the rotational vibration through the catheter shaft 14. The catheter shaft could optionally also include a high inertia region disposed proximal of the distal tip to stabilize the proximal portion of the catheter.

A further embodiment of the swivel joint 44 is a rotational bearing system. Additionally, the catheter 12 could be so flexible as to not require any special swivel connection. Any rotational oscillation would be damped along the length of the catheter shaft 14.

In addition to the guidewire 40 and the balloon 22, other embodiments of the catheter 12 include a linear reference transducer, and a rotational reference transducer. The balloon 22 is used with the balloon inflation/deflation system 38 to center the catheter 12 in a vessel lumen. The guidewire 40 is used to guide the catheter to the region to be imaged. The linear reference transducer is used when performing a three-dimensional pullback image of the vessel lumen. It allows for accurate determination of location axially along the lumen.

Further, the rotational reference transducer may be used to measure the rotational displacement between the catheter shaft 14 and the catheter tip 2. One embodiment is a Hall effect switch or other magnetic device where part of the device is attached to the catheter tip 2 and the remaining part of the device is attached to the catheter shaft 14. Signals are sent, via the wire bundle 20, containing tip 2 to shaft 14 displacement information. The information is processed and correlated with the ultrasound image. The reference transducers may also be made from strain-gauge type devices that change resistance with strain. Such strain gauge or reference transducers could be mounted across any part of the catheter that moves, including being mounted across the actuators to measure contraction and expansion.

Different therapeutic apparatus may be incorporated into a catheter bearing imaging capability. Endovascular treatment of patients is becoming more widely practiced and improved guidance of endovascular therapies would be beneficial to the patient. FIGS. 3, 6, 7, 8, 9, 15 and 16 illustrate some of the therapeutic apparatus applicable to this system.

Figure 6:
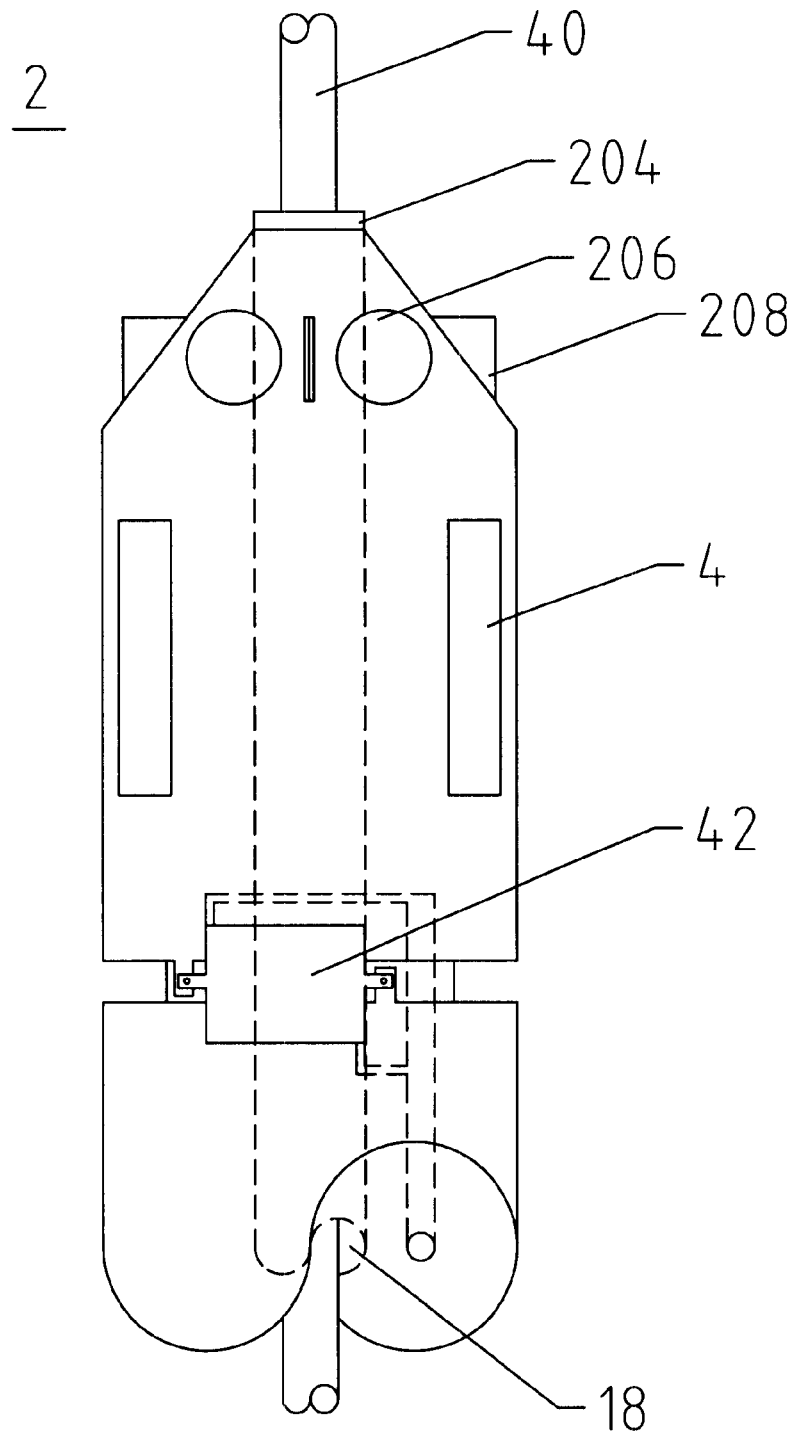
FIG. 6 is an enlarged view of the distal tip of the catheter of FIG. 3 illustrating cutting and suction apparatus for an atherectomy or thrombectomy system, according to aspects of an embodiment of the invention.

FIG. 6 shows an enlarged view of the distal tip 2 of catheter 12 with optional atherectomy or thrombectomy apparatus. Atherectomy and/or thrombectomy may be accomplished using a rotational or vibrating cutter disposed on the catheter to excise plaque or thrombus. The distal tip 2 additionally comprises the distal fluid-tight seal 204, the fluid suction ports 206 and the plurality of cutting apparatus 208. The cutting apparatus 208, such as cutting blades or atherectomy cutters, vibrate rotationally under the motion generated by actuator 42. Optionally, the cutting apparatus 208 may be driven by a different actuator than that used to drive the motion of the ultrasound arrays 4 and 202. The distal fluid-tight seal 204 prevents flow around the guidewire 40 exit when vacuum is generated in the central lumen 18. It allows the vacuum to be directed through vacuum ports 206 to remove tissue that has been excised by the cutting blades 208. Referring to FIG. 3, connector 226 seals the central lumen 18 around the guidewire 40 entrance using the proximal fluid-tight seal 242, and allows for connection of the vacuum source or suction device 224.

Figure 7:
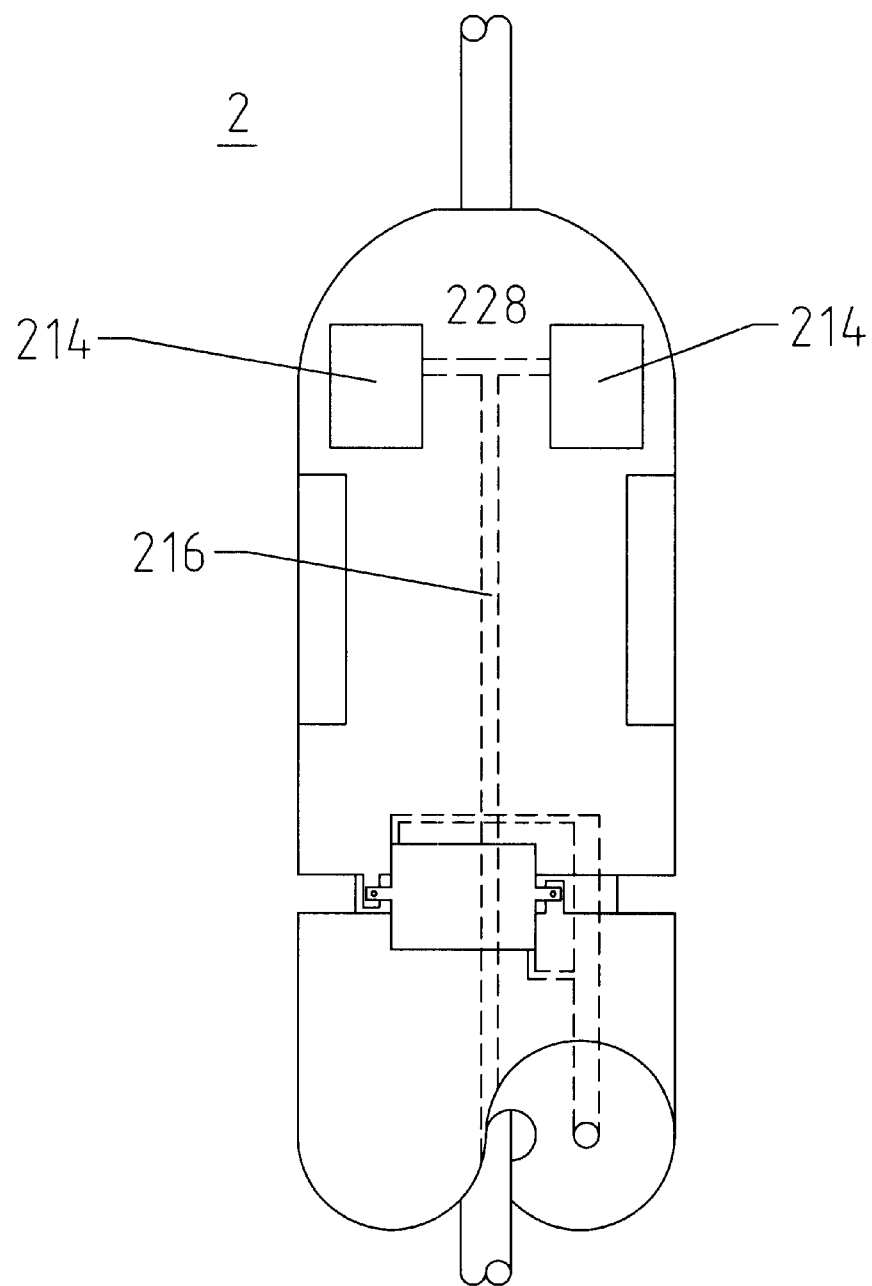
FIG. 7 is an enlarged view of the distal tip of the catheter of FIG. 3 illustrating a radio frequency, X-ray or microwave wave source, according to aspects of an embodiment of the invention.

FIG. 7 shows an enlarged view of distal tip 2 incorporating an optional wave source 228. These wave sources emit potentially therapeutic energy to the body lumen or cavity. The wave source 228 comprises a wave generator 214 and a plurality of electrical leads 216. Possible wave generators are an X-ray source such as an X-ray tube, a radio frequency antenna or a microwave antenna. Referring to FIG. 3 and FIG. 7, the electrical leads 216 are connected to the wave generator 214 at the distal tip 2, traverse the catheter 12 through the wire bundle 20 and are connected to the power source 220 at the proximal end 16 of catheter 12.

Figure 8:
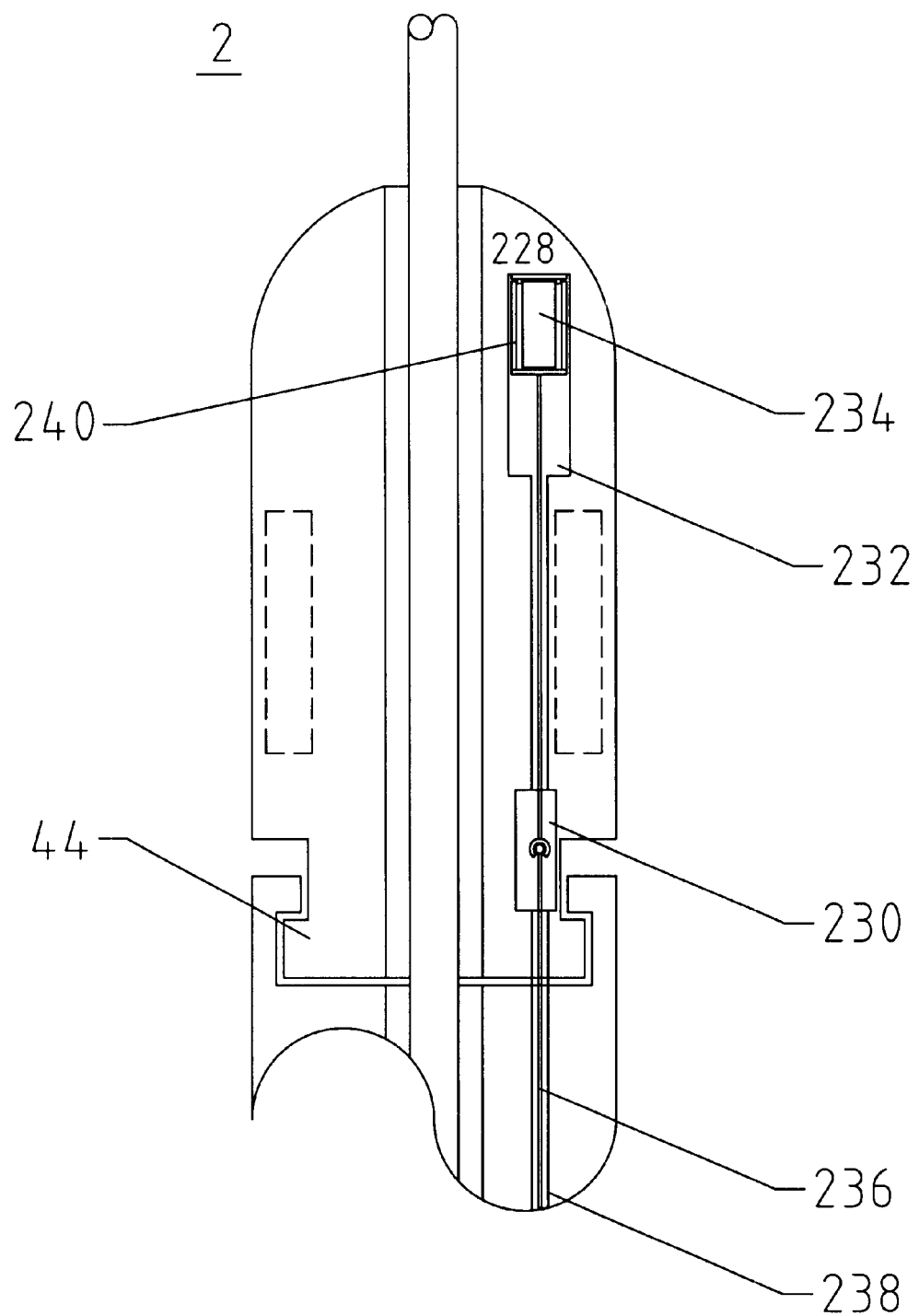
FIG. 8 is an enlarged sectional view of the distal tip of the catheter of FIG. 3 illustrating an ionizing radiation source and an optional shield or shutter, according to aspects of an embodiment of the invention.

FIG. 8 shows an enlarged sectional view of the distal tip 2 showing another embodiment of the optional wave source 228. In this embodiment, the optional wave source 228 comprises a radioactive source 234, a shutter 240, a cavity 232, a linkage 236, a flexible connector 230 and a lumen 238. The radioactive source 234 provides therapeutic energy, in the form of ionizing radiation, to the body vessel or lumen. The shutter 240 is opened and closed by linkage 236. When the shutter 240 is opened, the radioactive source 234 radiates outward into the body vessel or lumen. When the shutter 240 is closed, the radiation is prevented from escaping. The cavity 232 provides space for the shutter 240 to open. The linkage 236 rides within lumen 238 and is connected across the swivel joint 44 by the flexible connector 230. Referring to FIG. 3 and FIG. 8, the linkage 236 is connected at the proximal end 16 of catheter 12 to the shutter controller 222. The radioactive source 234 could be positioned proximal to the swivel joint 44 to eliminate the need for the flexible connector 230.

Figure 9:
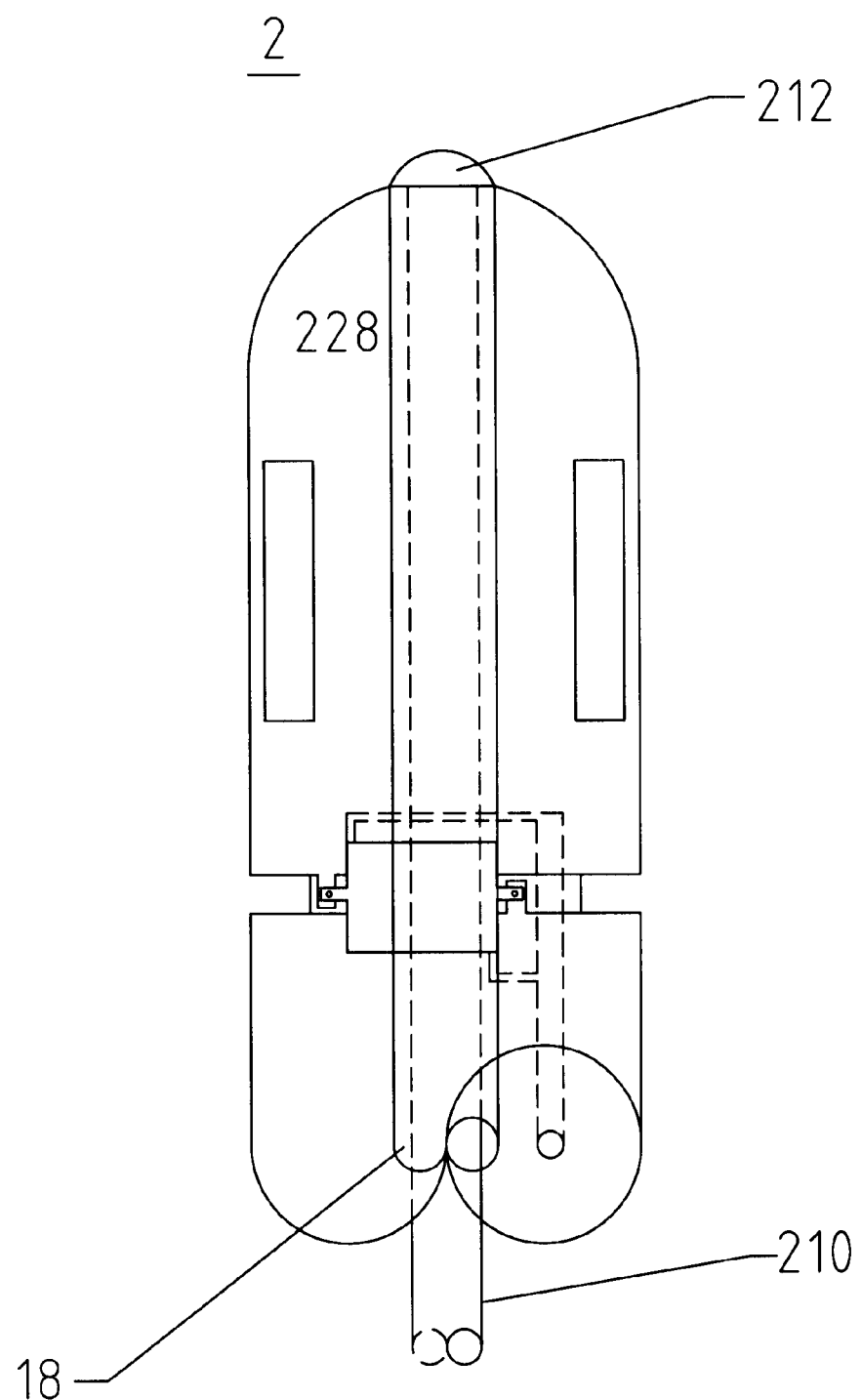
FIG. 9 is an enlarged view of the distal tip of the catheter of FIG. 3 illustrating a fiber-optic transmission system, according to aspects of an embodiment of the invention.

FIG. 9 shows an enlarged view of the distal tip 2 of catheter 12 comprising yet another embodiment of optional wave source 228. Wave source 228 comprises, in this embodiment, an optional fiber optic bundle 210 and a lens 212. The fiber optic bundle 210 is used to provide illumination of the body lumen or cavity with visible or near visible light such as infrared or ultraviolet light. The fiber optic bundle 210 is connected to the optional lens 212 to allow for focusing or dispersion of the light as desired. Referring to FIG. 3 and FIG. 9, the fiber optic bundle 210 is disposed along the central lumen 18 of the catheter 12, so that it is not stressed or flexed by the vibrational rotation of the catheter distal tip 2. The fiber optic bundle 210 is connected at the proximal end 16 of catheter 12 to the illumination source 218.

Figure 10:
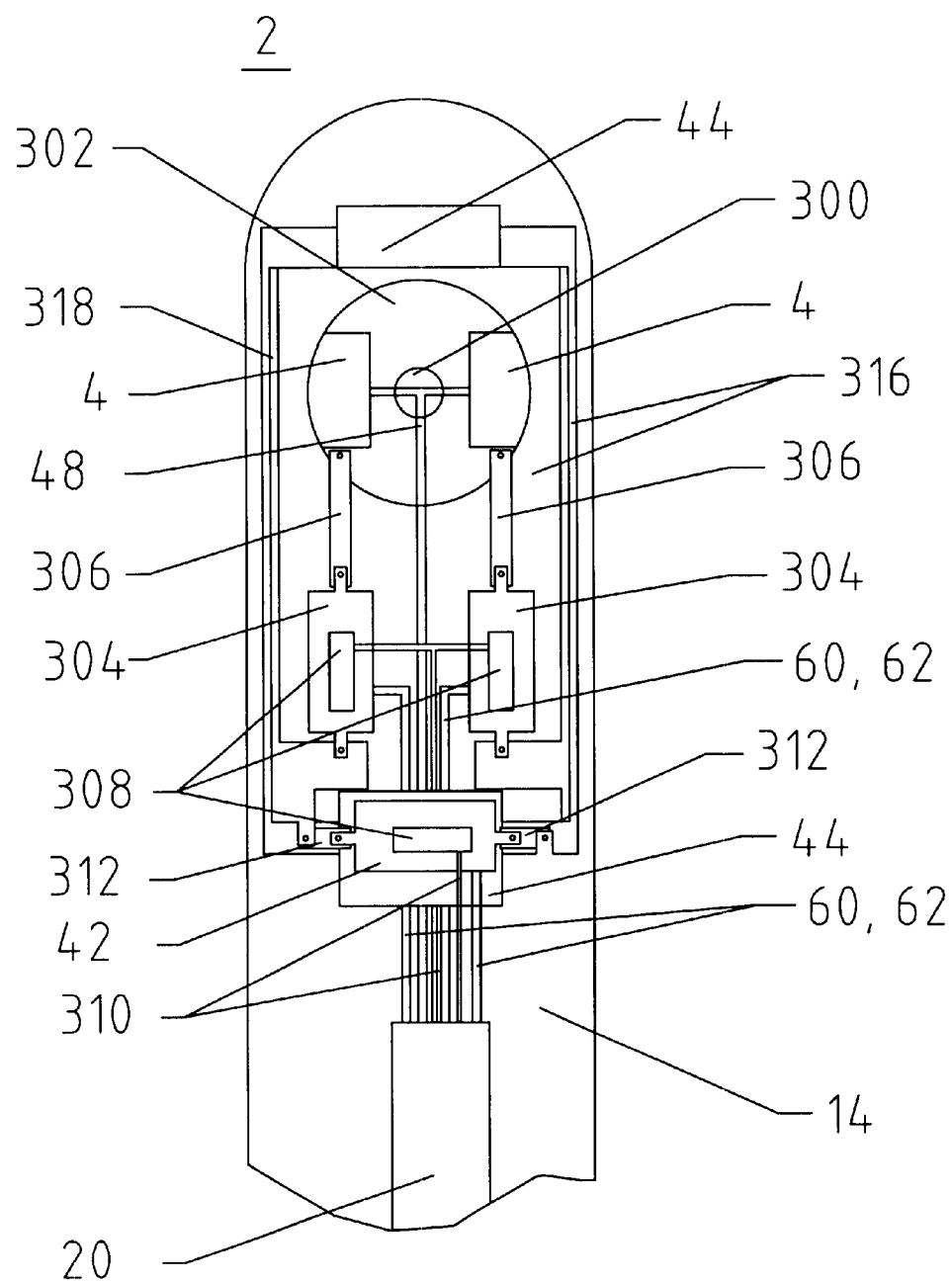
FIG. 10 is a sectional view of the distal tip of a catheter with an imaging array comprising an ultrasound transducer, which is oscillating circumferentially as well as axially, according to aspects of an embodiment of the invention.

FIG. 10 shows an enlarged view of the distal tip 2 of catheter 12 comprising elements that allow for three-dimensional imaging of the body lumen or cavity. The distal tip 2 comprises the catheter shaft 14, an axial carrier element 302, the array of radially outwardly directed ultrasound transducers 4, a circumferential carrier 318, an acoustic transmission fluid 316, an axial bearing 300, the circumferential rotational bearings or swivel joints 44, a set of at least one axial actuator 304, a corresponding set of axial connector arms 306, the circumferential actuators 42, a corresponding set of circumferential connector arms 312, a set of strain gauges 308 and the wire bundle 20.

As discussed previously, each array of ultrasound transducers 4 comprise the plurality of transducer leads 48. The circumferential actuators 42 and the axial actuators 304 comprise the positive signal/power leads 60 and the negative signal/power leads 62. The strain gauges 308 comprise a plurality of strain gauge electrical leads 310. The leads 48, 60, 62 and 310 are bundled together in the wire bundle 20 which travels the length of the catheter shaft 14 and carries power to the circumferential actuators 42 and the axial actuators 304 and power/deflection information to and from the strain-gauges 308 as well as output and reflection electrical signals to and from the ultrasound acoustic transducer array 4.

Referring to FIG. 10, the axial carrier element 302 holds the transducer array 4 within the circumferential carrier 318. The acoustic transmission fluid 316, such as water, fills the space between axial carrier 302 and circumferential carrier 318 as well as the space between circumferential carrier 318 and catheter shaft 14. The bearing 300 couples the axial carrier element 302 to the circumferential carrier 318. Circumferential rotational bearings 44 couple the circumferential carrier 318 to the catheter shaft 14. Axial actuators 304 connect the circumferential carrier 318 to the rotational carrier 302 through the axial connector arms 306. Circumferential actuators 42 connect the catheter shaft 14 to the circumferential carrier 318 through circumferential connector arms 312. Strain gauges 308 are connected across actuators 42 and 304.

Electrical signal leads 48 connect the ultrasound transducers 4 to wire bundle 20 through swivel joint 44. Positive signal/power leads 60 and negative signal/power leads 62 connect the axial actuators 304 and circumferential actuators 42 to the wire bundle 20 through swivel joint 44. Strain gauge electrical leads 310 connect the strain gauges 308 to the wire bundle 20 through swivel joint 44.

Referring to FIG. 3 and FIG. 10, axial carrier 302 holds the transducers 4 and is able to move in a rocking fashion around the axis constrained by bearing 300 to motion in the plane parallel to the axis of the catheter shaft 14. Bearing 300 is also an optional electrical swivel joint. Axial actuators 304 move the axial carrier 302 about bearing 300 to image in the forward (toward the distal tip) and backward (toward the proximal end of the catheter) direction. Sufficient space must be provided inside circumferential carrier 318 to allow for the desired motion of axial carrier 302. Acoustic transmission fluid 316 is required to fill any air gaps that might exist in the catheter tip so that the acoustic signals are not attenuated after leaving transducers 4 or before being received by transducers 4. The shapes of the circumferential carrier 318 and axial carrier 302 are designed to minimize drag and cavitation when operating in the liquid 316. Preferred shapes for the carriers 302 and 318 are cylinders with axes parallel to their respective bearings 300 and 44 or a single sphere. The sphere could be magnetically levitated within a cavity so no bearing would be needed. Optional connector arms 306 increase the freedom of motion for the axial carrier 302. Sufficiently flexible actuators 304 and 42 would not require connector arms 306 or 312, respectively. Strain gauges 308 provide positioning information for each of the actuators 304 and 42. The strain gauge 308 information is fed through the electrical lead 310, the swivel joint 44 and the wire bundle 20 to the decoder/processor 26 for image analysis. Positioning information is required in order to map the transducer output into a two or three-dimensional coordinate system. Actuators 42 move the circumferential array carrier 318 in the circumferential direction with one rotational bearing 44 shown near the tip of the catheter and another rotational bearing 44 located at the bottom of the circumferential carrier 318. Positive signal/power leads 60 and negative signal/power leads 62 provide controlled power to each of the actuators 304 and 42 through wire bundle 20 from actuator power supply/controller 30. Transducer leads 48, bearing 300 and electrical swivel joint 44 connect the decoder/processor 26 and ultrasound-input signal and power supply/controller 28 through the wire bundle 20 to the transducers 4.

Actuators 42 and 304 are shown for ease of viewing in the plane parallel to the axis of the catheter shaft 14. One or more actuators 42 and 304 could also be mounted in the plane perpendicular to the axis of the catheter shaft 14. One or both sets of actuators 304 and 42 could be disposed on a single integrated device to provide motion in both the circumferential and the forward and backward axial rocking directions. Such orthogonal disposition of some or all the actuators could minimize longitudinal stiffness in the catheter and maximize flexibility. In addition, swivel bearings 300 and 44 could be replaced with a single bearing operational in two dimensions, rotation and axial. Such a bearing would be, for example, a ball in a socket or an elastic coupling. The axial transducer carrier 302 and the circumferential transducer carrier 318 would be integrated into a single unit for the single bearing system. In a further evolved embodiment, the transducers 4 could be mounted to actuators 304 and 42 such that no pivot bearing is required, rather, the transducers 4 would be pivoted directly by the actuators. The transducers 4 could also be moved linearly by the actuators but motion is limited by the travel of the actuators so pivoting allows for increasing the three-dimensional imaging volume without a very large amount of actuator travel. The apparatus allows for two-dimensional and three-dimensional imaging of a body lumen or cavity without the need to move the catheter shaft 14 to obtain some of the imaging information.

In a preferred embodiment, actuators 304 and 42 would be nitinol actuators. These actuators 304 and 42 operate independently to move their respective carriers 302 and 318 about their respective pivot points. Each actuator is separately operated or fired. Counter-attached actuators 304 are energized sequentially to create a rocking motion of the axial carrier 318, around axial bearing 300, through axial connector arms 306. This axial rocking motion is independent of the circumferential rocking motion generated by actuators 42. Counter-attached actuators 42 would be energized sequentially to create a rocking motion of circumferential carrier 318, around circumferential bearing 44, through circumferential connector arms 312. Sequential energizing of counter-attached actuators involves energizing one actuator while power to the other actuator is turned off. Various types of motion could be obtained with this system ranging from random motion to a coordinated scan similar to that used on cathode ray tube screens. Circumferential and axial scan rates of 1 to 400 Hz are appropriate with preferred ranges of 30 to 200 Hz.

Figure 11:
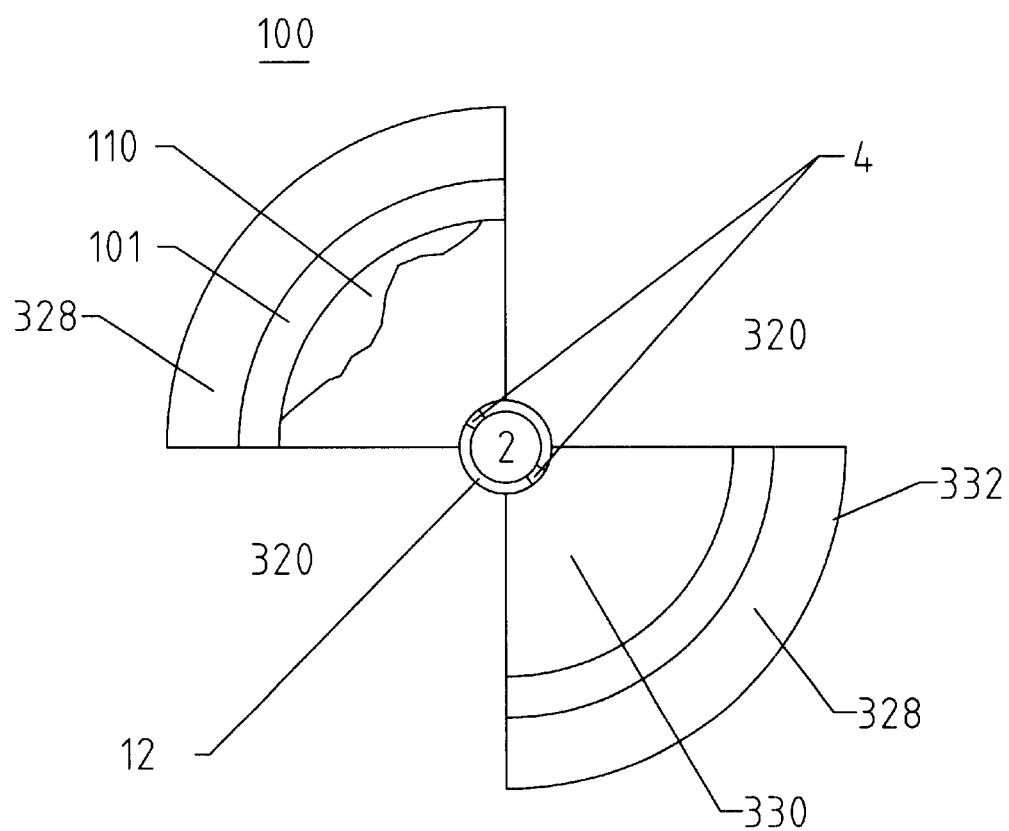
FIG. 11 illustrates the imaging area of a transducer oscillating circumferentially according to aspects of an embodiment of the invention.

FIG. 11 illustrates, in cross-section orthogonal to the axis of the catheter, the two-dimensional imaging area of a two-ultrasound transducer array 4, rotating or oscillating circumferentially through a 90-degree arc. Catheter 12 is inserted into body lumen 100. The tip 2 of catheter 12 comprises the array 4 of two ultrasound transducers. The image generated by the ultrasound transducer array 4 has a range illustrated by a boundary 332. Body lumen 100 comprises the body lumen wall 101, the surface irregularity or atherosclerosis 110, a surrounding tissue 328 and a volume of blood or fluid 330.

The lumen wall 101 is disposed circumferentially around catheter 12, which is centered in body lumen 100. In this embodiment, the array of transducers 4 is rotated or oscillated only in the circumferential direction through a 90-degree angle. A two-dimensional wedge shaped image of the body lumen 100 is obtained. The wedge is bounded by the range of the transducers 4 and the angle through which the transducers 4 are rotated. In this embodiment, the image area comprises two 90-degree wedges. Additionally, there is an area where no information is acquired comprising a blind area 320 of two 90-degree wedges. The body lumen wall 101, surface irregularity 110, surrounding tissue 328 and fluid 330 are not visible in the blind areas 320.

The maximum range of the transducers is described by the boundary 332. The distance from the transducer 4 to the boundary 332 and the resolution of the image are affected by the modulation frequency of the transducer array 4. In general, when the modulation frequency is increased, the range is decreased and the resolution of the image is increased. The modulation frequency of the ultrasound system is from 1 to 100 MHz, with a preferred range from 5 to 50 MHz and a more preferred range of 10 to 30 MHz. The practical circumferential angular limit is determined by the mechanics and dynamics of the actuators 42 and circumferential connector arms 312, number of transducers 4, mechanics of bearings 44 and 300 and the space available within the catheter 12.

Figure 12:
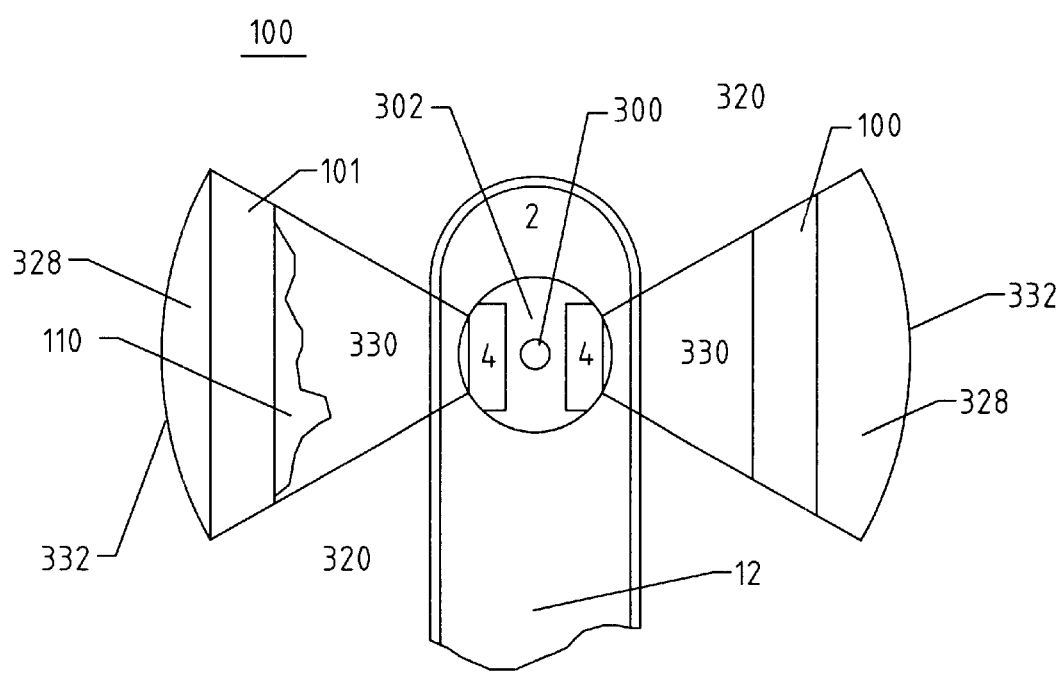
FIG. 12 illustrates the imaging area of a transducer oscillating longitudinally along the axis of the catheter, according to aspects of an embodiment of the invention.

FIG. 12 illustrates, in cross-section parallel to the axis of the catheter, the two-dimensional imaging area of a two-ultrasound transducer array 4 rocking or pivoting longitudinally parallel to the axis of the catheter through a 60-degree arc. Catheter 12 is inserted into body lumen 100. The tip 2 of catheter 12 comprises the array 4 of two ultrasound transducers in axial carrier 302 being rocked around axial bearing 300. Body lumen 100 comprises the surface irregularity or atherosclerosis 110, the surrounding tissue 328 and blood or fluid 330. Fluid 330 fills the image between the body lumen wall 101 and the catheter 12. The body lumen wall 101 is disposed around catheter 12, which is centered in the body lumen 100. In this embodiment, the array of transducers 4 is rocked 30 degrees forward and 30 degrees backward (60 degrees total) in the plane parallel to the axis of the catheter 12. A two-dimensional wedge-shaped image of the body lumen wall 101 is obtained. The wedge is bounded by the range 332 of the transducers 4 and the angle through which the transducers 4 are rocked. In this embodiment, the field of view or imaging area comprises two 60-degree wedges. Additionally there is an area where no information is acquired comprising the dead or blind area 320 of two 120-degree wedges. The body lumen wall 101, blood 330 and atherosclerosis 110 are not visible in the blind areas 320.

Referring to FIG. 3 and FIG. 10, the practical limit of the angular tilt of the array of transducers 4 is governed by the mechanics and dynamics of the bearing 300, the axial carrier 302, the space provided for the carrier 302 to move, the mechanics of the linkages 306 and the performance of the actuators 304. The practical angular limit in the plane parallel to the catheter 12 is 180 degrees or less. The practical range 332 of the system is governed by the frequency of the ultrasound signal and other characteristics of the transducers 4 and their controller 28 but is sufficient to visualize the body lumen 100 and immediate surroundings. These factors also have an effect on the resolution of the system.

Figure 13:
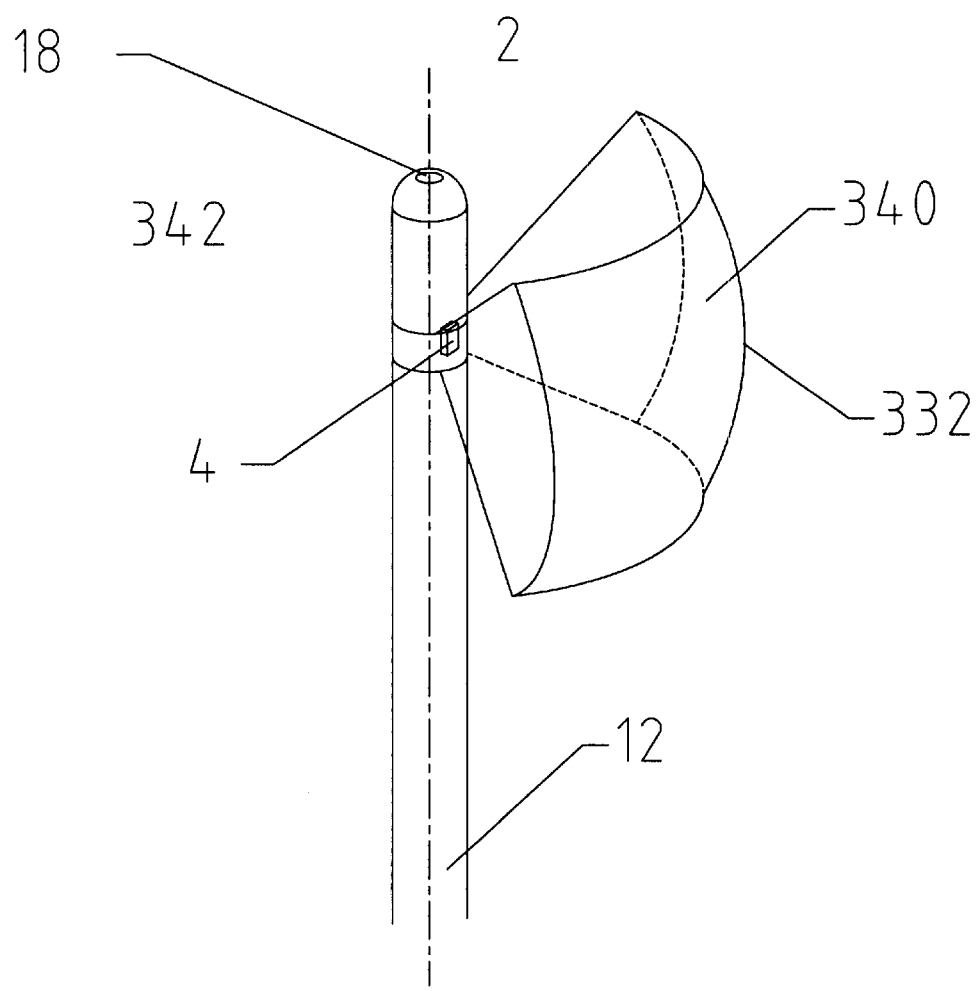
FIG. 13 illustrates the imaging volume of a single transducer array oscillating circumferentially approximately 90 degrees and axially approximately 60 degrees, according to aspects of an embodiment of the invention.

FIG. 13 illustrates the three-dimensional imaging volume of the single ultrasound transducer array 4, oscillating circumferentially through a 90-degree angle (45 degrees clockwise and 45 degrees counterclockwise) and simultaneously rocking through a 60-degree angle (30 degrees forward and 30 degrees backward). In this embodiment, the catheter 12 comprises the single transducer ultrasound array 4 and the central lumen 18. As the array 4 is rotated and rocked, a three-dimensional field of view or imaging volume 340 is obtained. The imaging volume 340 is bounded by the range 332 of the transducer array 4, two 90-degree wedges and two 60-degree wedges. Additionally, there is an area where no information is acquired comprising a dead or blind volume 342. The blind volume 342 is the sphere enclosing the array 4 with the range 332 minus the imaging volume 340. These representative specifications are appropriate to allow for monitoring of endovascular therapies. However, the angular specifications may significantly differ from those shown and still be useful and appropriate.

Figure 14:
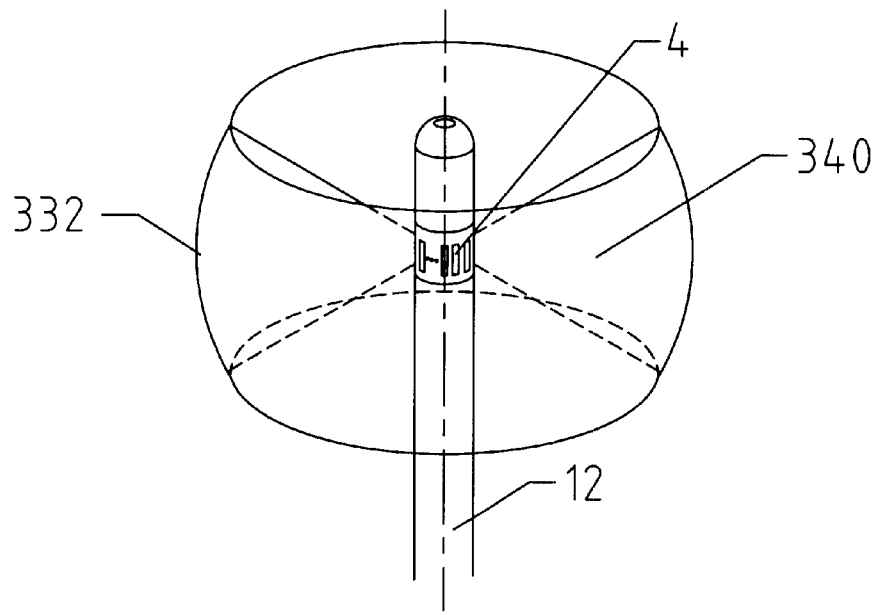
FIG. 14 illustrates the three-dimensional imaging volume of a transducer array of four transducers oscillating circumferentially 90 degrees and axially 60 degrees relative to the axis of the catheter, according to aspects of an embodiment of the invention.
Figure 14:
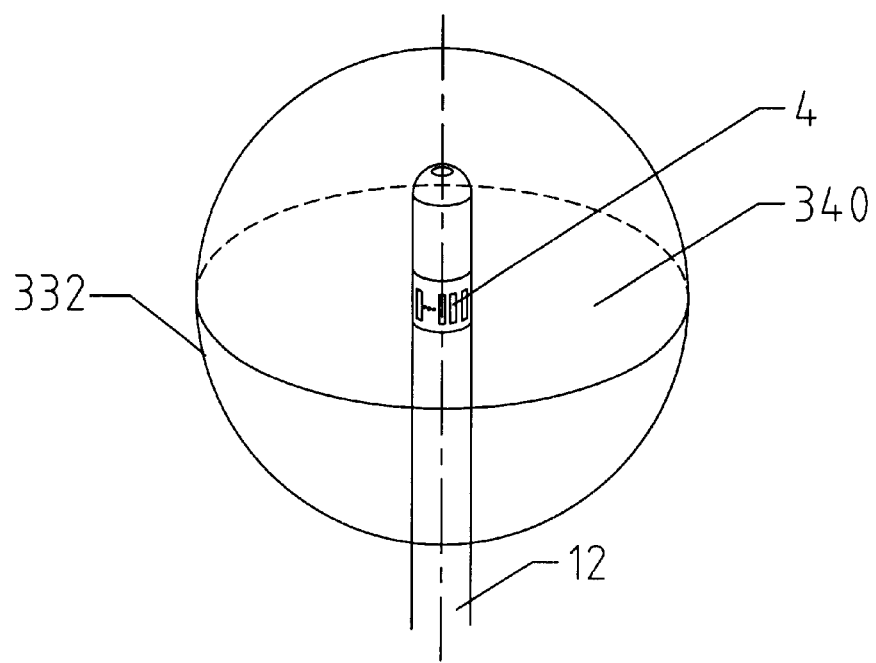

FIG. 14A illustrates the three-dimensional imaging volume 340 of catheter 12. In this embodiment, sufficient transducers 4 are rotated through a circumferential angle sufficient to fill in the gaps or blind zones between the transducers 4. For example, if four transducers 4 are used, a circumferential rotation angle of 90-degrees or greater would suffice to render a complete 360-degree image. Six transducers 4 would require a 60-degree or greater circumferential rotation angle. The array of ultrasound transducers 4 are also rocked or pivoted axially through a 60-degree angle. The resulting three-dimensional imaging volume 340 is a toroid bounded by the range 332 of the transducers 4 and constrained within a 60-degree wedge shaped longitudinal section.

FIG. 14B shows the three-dimensional imaging volume 340 of catheter 12 where axial rocking occurs through a greater angle than in FIG. 14A. In this embodiment, sufficient transducers 4 are rotated through a circumferential angle sufficient to fill in the gaps or blind zones between the transducers 4. Additionally, the transducer array 4 is rocked axially through a 180-degree angle. The resulting three-dimensional imaging volume 340 is a sphere centered about the ultrasound array 4 and bounded by the range 332 of the ultrasound transducers 4. In this embodiment, there are no blind zones within the range 332 of the transducers 4.

Figure 15:
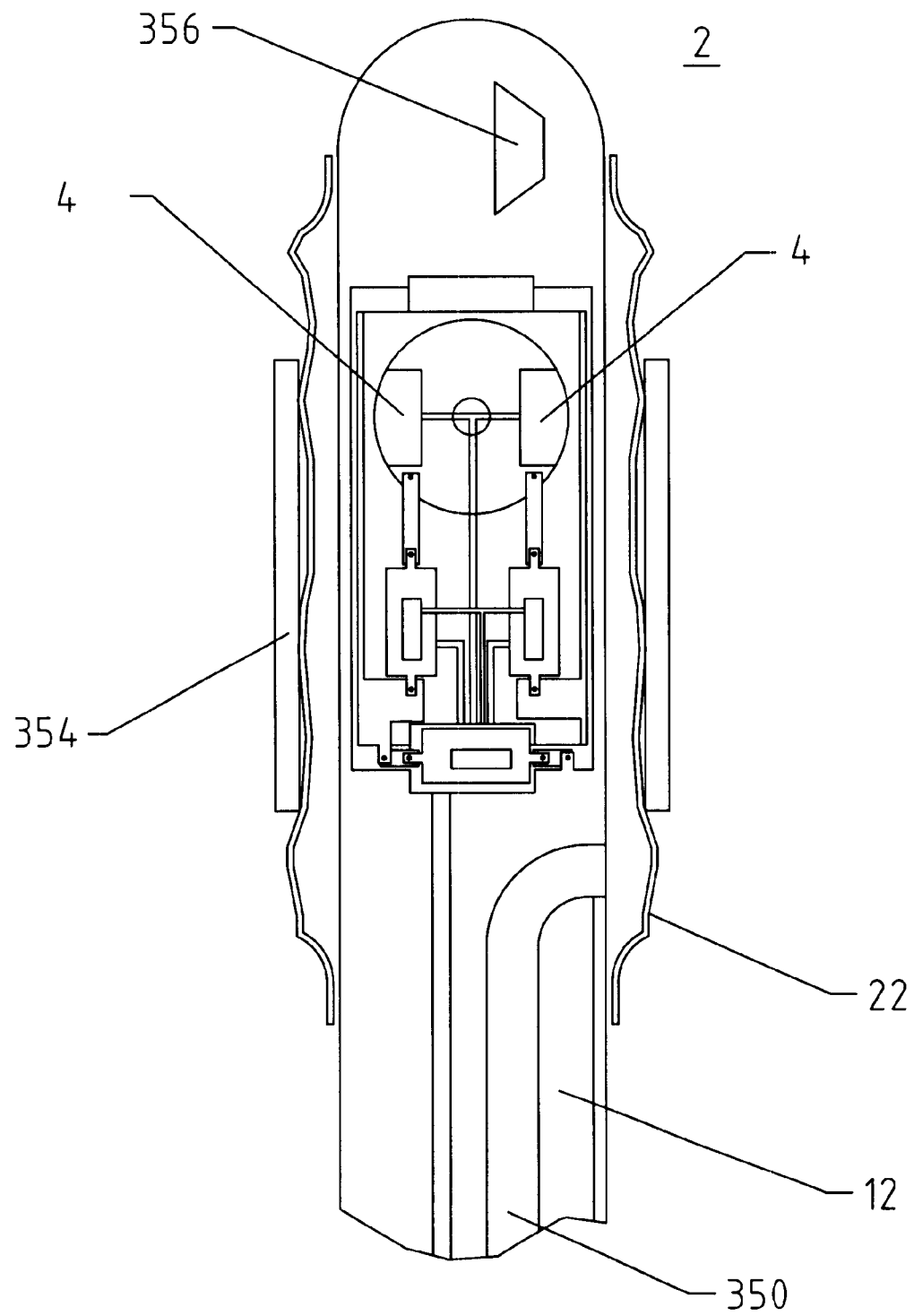
FIG. 15 is a sectional view of a catheter tip illustrating an inflation lumen, a collapsed dilatation balloon and a collapsed stent, according to aspects of an embodiment of the invention. The catheter also includes the transducer array and actuators for three-dimensional imaging of the body lumen or cavity.
Figure 16:
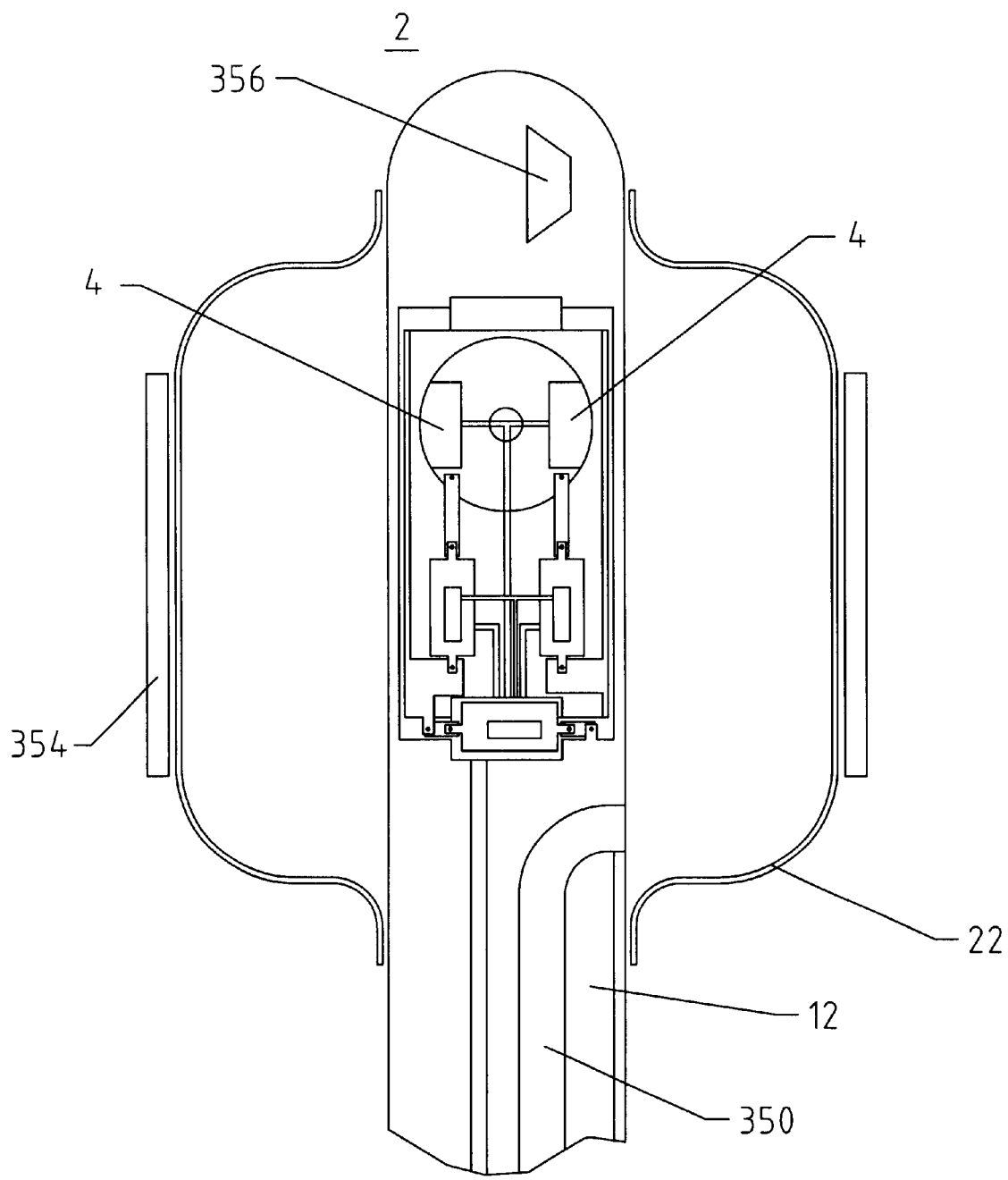
FIG. 16 is a view of the catheter tip of FIG. 15 with the dilatation balloon and stent expanded, according to aspects of an embodiment of the invention.

FIG. 15 and FIG. 16 show the tip 2 of the catheter 12 with the added features of the inflation lumen 350, the non-distensible dilatation balloon 22, a stent 354 and a radiopaque marker 356. Referring to FIG. 15, the balloon 22 and the stent 354 are collapsed to be able to pass through the body lumen 100 to the target site. In this embodiment, the balloon 22 is positioned on the catheter tip 2, over the transducer array 4, to be able to image the balloon 22 and stent 354 during inflation and deployment or retrieval. Deployment or retrieval of resiliently expandable stents 354 or devices would be similarly monitored with this system. The radiopaque marker 356 allows for visualization of the catheter under fluoroscopy and X-ray. The radiopaque marker 356 may be designed to provide orientation information for the catheter in the circumferential direction. Typically, the radiopaque marker 356 is fabricated from tantalum, platinum or the like.

FIG. 16 shows the tip 2 of the catheter 12 with the balloon 22 and the stent 354 expanded. Expansion occurs through the application of high-pressure fluid, preferably water, saline or radiopaque contrast material to the interior of the balloon 22, which is accessed by the inflation lumen 350. Referring to FIG. 3 and FIG. 16, the high pressure is generated by the inflation system 38, such as a syringe, connected at the proximal end 16 of the catheter 12 to the inflation port 36, which connects to the balloon 22 through the inflation lumen 350.

The present invention may be embodied in other specific forms without departing from its spirit or essential characteristics. The described embodiments are to be considered in all respects only as illustrative and not restrictive. The scope of the invention is therefore indicated by the appended claims rather than the foregoing description. All changes which come within the meaning and range of equivalency of the claims are to be embraced within their scope.

I claim:

1. An imaging device for emitting ultrasonic acoustic waves and providing a useable image in response to detection of reflections of said ultrasonic acoustic waves, said imaging device comprising:

an axially elongate structure adapted for insertion into a body lumen or cavity;

an array of radially, outwardly directed transmitting transducer elements mounted to said axially elongate structure for electrically generating a plurality of output ultrasonic waves;

at least one primary actuator operably connected to said axially elongate structure, at or near its distal end, for rotationally vibrating said array of radially, outwardly directed transmitting transducer elements;

a cable connecting said axially elongate structure to an environment external of said body lumen or cavity and including at least one signal channel for transporting electrical signals;

at least one receiving transducer element mounted on said axially elongate structure and proximate to said array of transmitting transducer elements for receiving reflections of said output ultrasonic acoustic waves from said array of transmitting transducer elements and converting said reflections of said output ultrasonic acoustic waves to reflection electrical signals that may be transmitted along at least one of said signal channels in said cable;

a processor responsive to said reflection electrical signals from said cable for providing imaging data from said reflection electrical signals; and a display responsive to said imaging data for providing a visual image of said body lumen or cavity and surrounding structures.

2. The apparatus of claim 1 wherein the axially elongate structure comprises apparatus adapted for performing endovascular therapy.

3. The apparatus of claim 2 wherein the axially elongate structure is adapted to monitor the endovascular therapy using the array.

4. The apparatus of claim 1 wherein said axially elongate structure comprises an inflatable balloon and at least one lumen for inflation and deflation of said balloon.

5. The apparatus of claim 1 wherein said axially elongate structure comprises a lumen for passage of a guidewire.

6. The apparatus of claim 1 wherein said axially elongate structure comprises a stent.

7. The apparatus of claim 1 wherein said axially elongate structure further comprises apparatus for addition or removal of foreign bodies, fluids, or materials from the body lumen or cavity.

8. The apparatus of claim 1 further comprising a second actuator, operably connected to said axially elongate structure, to vibrate the radially, outwardly directed transducer array about an axis different than that of the primary actuator.

9. The apparatus of claim 1 further comprising apparatus to map a three-dimensional image onto a two-dimensional monitor.

10. The apparatus of claim 1 wherein said transmitting transducer elements and said receiving transducer elements are the same physical entity.

11. The apparatus of claim 1 further comprising a forwardly directed array of transducer elements.

12. The apparatus of claim 1 wherein said actuator is constructed from shape-memory materials.

13. The apparatus of claim 1 wherein said actuator is comprised of nitinol.

14. A method of imaging characteristics of a body lumen or cavity and surrounding structure using a catheter assembly comprising a catheter shaft, a radial scanning array of outwardly directed transducer elements, located at the end of a transmission line, and at least one actuator, operably connected near the distal end of said catheter shaft, said method comprising the steps of:

inserting said catheter assembly into said body lumen or cavity;

emitting ultrasonic signals into said body lumen or cavity and surrounding structure by selectively exciting at least one of said transducer elements;

rotationally oscillating said array of transducer elements to intermediate scan positions with respect to an initial imaging position, the oscillation being in the circumferential direction, relative to a distal region of said catheter shaft, using said at least one actuator;

receiving reflections of said ultrasonic signals impinging on at least one of said transducer elements;

converting said reflections of said ultrasonic signals to reflection electrical signals suitable for transmission on said transmission line;

transmitting said reflection electrical signals on said transmission line to an area external to said body lumen or cavity;

processing said reflection electrical signals into image data; and using said image data to guide said catheter so as to perform atherectomy, thrombectomy, stent or material delivery, stent or material removal, angioplasty, drug delivery, or radiation therapy of the body lumen or cavity.

15. The method of claim 14 wherein said method further comprises the step of displaying said image data on a visual display.

16. The method of claim 14 wherein said method further comprises the step of displaying said image data in real time.

17. The method of claim 14 wherein the shaft of said catheter assembly is substantially stationary with respect to the surrounding body lumen or cavity during an imaging process.

18. The method of claim 14 wherein the radial scanning array of outwardly directed transducer elements are further rocked or pivoted in a plane parallel to a longitudinal axis of the catheter shaft, using a second actuator.

19. The method of claim 18 further comprising mapping a three-dimensional image onto a two dimensional monitor.

20. A method of imaging characteristics of a body lumen or cavity and surrounding structure using a catheter assembly comprising a catheter shaft, a radial scanning array of outwardly directed transducer elements located at the end of a transmission line, and at least one primary actuator operably connected near the distal end of said catheter shaft, said method comprising the steps of:

inserting said catheter assembly into said body lumen or cavity;

emitting ultrasonic signals into said body lumen or cavity and surrounding structure by selectively exciting at least one of said transducers elements;

rotationally oscillating said array of transducer elements to intermediate scan positions with respect to an initial imaging position, the oscillation being in the circumferential direction, relative to a distal region of said catheter shaft, wherein the at least one primary actuator rotationally oscillates said array of transducer elements;

rocking or pivoting said array of transducer elements in a plane parallel to a longitudinal axis of the catheter shaft, wherein a second actuator rocks or pivots said array of transducer elements;

receiving reflections of said ultrasonic signals impinging on at least one of said transducer elements;

converting said reflections of said ultrasonic signals to reflection electrical signals suitable for transmission on said transmission line;

transmitting said reflection electrical signals on said transmission line to an area external to said body lumen or cavity; and processing said reflection electrical signals into real time three-dimensional image data.

21. The method of claim 20 wherein acquisition of the image data is substantially independent of motion of the shaft of said catheter.

* * * * *